US008124349B2

(12) United States Patent
Latz et al.

(10) Patent No.: US 8,124,349 B2
(45) Date of Patent: Feb. 28, 2012

(54) TOLL-LIKE RECEPTOR ASSAYS

(75) Inventors: Eicke Latz, Shrewsbury, MA (US);
Alberto Visintin, Worcester, MA (US);
Douglas T. Golenbock, Wellesley, MA (US)

(73) Assignee: University of Massachusetts, Shrewsbury, MA (US)

( * ) Notice: Subject to any disclaimer, the term of this patent is extended or adjusted under 35 U.S.C. 154(b) by 212 days.

(21) Appl. No.: 11/326,963

(22) Filed: Jan. 6, 2006

(65) Prior Publication Data

US 2006/0099650 A1     May 11, 2006

Related U.S. Application Data

(63) Continuation of application No. 11/014,351, filed on Dec. 16, 2004, now abandoned.

(60) Provisional application No. 60/530,115, filed on Dec. 16, 2003, provisional application No. 60/530,699, filed on Dec. 16, 2003.

(51) Int. Cl.
*G01N 33/53* (2006.01)
*G01N 33/00* (2006.01)
*C12Q 1/66* (2006.01)
*C12P 21/04* (2006.01)
*C07K 1/00* (2006.01)
*C07K 14/00* (2006.01)

(52) U.S. Cl. .......... 435/7.1; 435/7.2; 435/7.5; 435/7.92; 435/8; 435/69.7; 530/350; 530/402

(58) Field of Classification Search .................. None
See application file for complete search history.

(56) References Cited

U.S. PATENT DOCUMENTS

| | | | | |
|---|---|---|---|---|
| 5,556,748 | A | 9/1996 | Douglas | 435/6 |
| 7,220,723 | B2 * | 5/2007 | Tracey et al. | 514/12 |
| 7,271,248 | B2 * | 9/2007 | Hardiman et al. | 530/387.1 |
| 7,388,080 | B2 * | 6/2008 | Kurt-Jones et al. | 530/388.1 |
| 2003/0027260 | A1 * | 2/2003 | Goddard et al. | 435/69.1 |
| 2003/0100031 | A1 * | 5/2003 | Dower et al. | 435/7.9 |
| 2003/0104523 | A1 | 6/2003 | Bauer et al. | 435/69.1 |
| 2005/0186662 | A1 * | 8/2005 | Low | 435/69.4 |

FOREIGN PATENT DOCUMENTS

WO     WO 96/39411     12/1996

OTHER PUBLICATIONS

Dickson et al. 1995. J. of Photochem and Photobiology B:Biology 27:3-19.*
Lawton et al. 2003. Current Opinion in Chem Biol. 7:446-451.*
Marshak-Rothstein. 2006. Nature Rev, Immunology 6:823-835.*
Tsien 1998. Ann Rev of Biochem. 67:509-44.*
Christopoulous et al. 2002. Pharm Reviews 54:323-374.*
Spohn communication Jul. 8, 2009.*
Tools for TLR research 2003.pdf.*
Massari et al. 2002 J. Immunology 168:1533-1537.*
Takeuchi et al 2002. J. Immunology 169:10-14.*
Pollock et al. 1999. Trends in Cell Biology 9:57-60.*
Agrawal and Kandimalla, "Medicinal chemistry and therapeutic potential of CpG DNA," Trends Mol. Med. 8(3):114-21 (2002).
Anders et al., "Activation of toll-like receptor-9 induces progression of renal disease in MRL-Fas(lpr) mice," FASEB J. 18(3):534-6 (2004).
Banchereau et al., "Immunobiology of dendritic cells," Annu. Rev. Immunol. 18:767-811 (2000).
Bell et al., "Leucine-rich repeats and pathogen recognition in Toll-like receptors," Trends Immunol. 24(10):528-33 (2003).
Beutler, "Inferences, questions and possibilities in Toll-like receptor signaling," Nature 430(6996):257-63 (2004).
Compton et al., "Human cytomegalovirus activates inflammatory cytokine responses via CD14 and Toll-like receptor 2," J. Virol. 77(8):4588-96 (2003).
Fitzgerald et al., "LPS-TLR4 signaling to IRF-3/7 and NF-kappaB involves the toll adapters TRAM and TRIF," J. Exp. Med. 198(7):1043-55 (2003). Epub Sep. 29, 2003.
Flo et al., "Involvement of toll-like receptor (TLR) 2 and TLR4 in cell activation by mannuronic acid polymers," J. Biol. Chem. 277(38):35489-95 (2002).
Hyakushima et al., "Interaction of soluble form of recombinant extracellular TLR4 domain with MD-2 enables lipopolysaccharide binding and attenuates TLR4-mediated signaling," J. Immunol. 173(11):6949-54 (2004).
Ingalls et al., "CD11/CD18 and CD14 share a common lipid A signaling pathway," J. Immunol. 161(10):5413-20 (1998).
Janssens and Beyaert, "Role of Toll-like receptors in pathogen recognition," Clin. Microbiol. Rev. 16(4):637-46 (2003).
Latz et al., "Lipopolysaccharide rapidly traffics to and from the Golgi apparatus with the toll-like receptor 4-MD-2-CD14 complex in a process that is distinct from the initiation of signal transduction," J. Biol. Chem. 277(49):47834-43 (2002).
Latz et al., "TLR9 signals after translocating from the ER to CpG DNA in the lysosome," Nat. Immunol. 5(2):190-8 (2004).
Leadbetter et al., "Chromatin-IgG complexes activate B cells by dual engagement of IgM and Toll-like receptors," Nature 416(6881):603-7 (2002).
LeBouder et al., "Soluble forms of Toll-like receptor (TLR)2 capable of modulating TLR2 signaling are present in human plasma and breast milk," J. Immunol. 171(12):6680-9 (2003).
Lien et al., "Toll-like receptor 4 imparts ligand-specific recognition of bacterial lipopolysaccharide," J. Clin. Invest. 105(4):497-504 (2000).
Ligoxygakis et al., "Activation of *Drosophila* Toll during fungal infection by a blood serine protease," Science 297(5578):114-6 (2002).
Massari et al., "Cutting edge: Immune Stimulation by Neisserial Porins is Toll-like Receptor 2 and MyD88 Dependent," J. Immunol. 168:1533-37 (2002).
Meng et al., "Antagonistic antibody prevents toll-like receptor 2-driven lethal shock-like syndromes," J. Clin. Invest. 113(10):1473-81 (2004).

(Continued)

*Primary Examiner* — Shulamith H Shafer
(74) *Attorney, Agent, or Firm* — Fish & Richardson P.C.

(57) ABSTRACT

Methods of identifying compounds that modulate the interaction between a TLR and a molecule that interacts with the TLR by direct binding or by inclusion in a complex that associates with the TLR are described. Methods of identifying molecules that interact with a TLR are also described.

14 Claims, 6 Drawing Sheets

OTHER PUBLICATIONS

Oxenius et al., "CpG-containing oligonucleotides are efficient adjuvants for induction of protective antiviral immune responses with T-cell peptide vaccines," J. Virol. 73(5):4120-6 (1999).

Pancer et al., "Somatic diversification of variable lymphocyte receptors in the agnathan sea lamprey," Nature 430(6996):174-80 (2004).

Poltorak et al., "Physical contact between lipopolysaccharide and toll-like receptor 4 revealed by genetic complementation," Proc. Natl. Acad. Sci. USA 97(5):2163-7 (2000).

Pugin et al., "Soluble MD-2 activity in plasma from patients with severe sepsis and septic shock," Blood 104(13):4071-9 (2004).

Sandor et al., "Importance of extra- and intracellular domains of TLR1 and TLR2 in NFkappa B signaling," J. Cell Biol. 162(6):1099-110 (2003).

Sau et al., "The antifungal drug amphotericin B promotes inflammatory cytokine release by a Toll-like receptor- and CD14-dependent mechanism," J. Biol. Chem. 278(39):37561-8 (2003).

Schjetne et al., "Cutting edge: link between innate and adaptive immunity: Toll-like receptor 2 internalizes antigen for presentation to CD4+ T cells and could be an efficient vaccine target," J. Immunol. 171(1):32-632 2004 (2003).

Takeshita et al., "Cutting edge: Role of Toll-like receptor 9 in CpG DNA-induced activation of human cells," J. Immunol. 167(7):3555-8 (2001).

van der Kleij et al., "A novel host-parasite lipid cross-talk. Schistosomal lyso-phosphatidylserine activates toll-like receptor 2 and affects immune polarization," J. Biol. Chem. 277(50):48122-9 (2002).

Visintin et al., "Lysines 128 and 132 enable lipopolysaccharide binding to MD-2, leading to Toll-like receptor-4 aggregation and signal transduction," J. Biol. Chem. 278(48):48313-20 (2003).

Walport, "Complement. First of two parts," N. Engl. J. Med. 344(14):1058-66 (2001).

Weber et al., "Binding of the *Drosophila* cytokine Spatzle to Toll is direct and establishes signaling," Nat. Immunol. 4(8):794-800 (2003).

Wyllie et al., "Evidence for an Accessory Protein Function for Toll-Like Receptor 1 in Anti-Bacterial Responses," J. Immunol. 165:7125-132 (2000).

Zuany-Amorim et al., "Toll-like receptors as potential therapeutic targets for multiple diseases," Nat. Rev. Drug Discov. 1(10):797-807 (2002).

Scorilas, A., Bjartell, A., Lilja, H., Moller, C., Diamandis, E.P. Streptavidin-Polyvinylamine Conjugates Labeled with a Europium Chelate: Applications in Immunoassay, Immunohistochemistry, and Microarrays. Clinical Chemistry. 46(9):1450-1455.2000.

Bieback et al., "Hemagglutinin protein of wild-type measles virus activates toll-like receptor 2 signaling," J. Virol., 76(17):8729-8736, (2002).

* cited by examiner color reaction
anti-mouse HRP
anti-GFP

TLR-GFP biotinylated ODN
neutravidin color reaction
streptavidin-HRP
biotinylated ODN

TLR-GFP anti-GFP

TR-fluorescence
anti-GFP-Europium

TLR-GFP biotinylated ODN
neutravidin

TR-fluorescence
streptavidin-Europium
biotinylated ODN

TLR-GFP anti-GFP

Fig. 3A
Fig. 3B
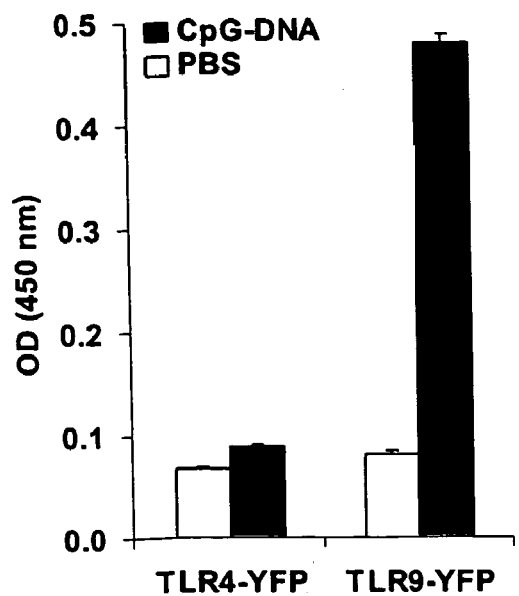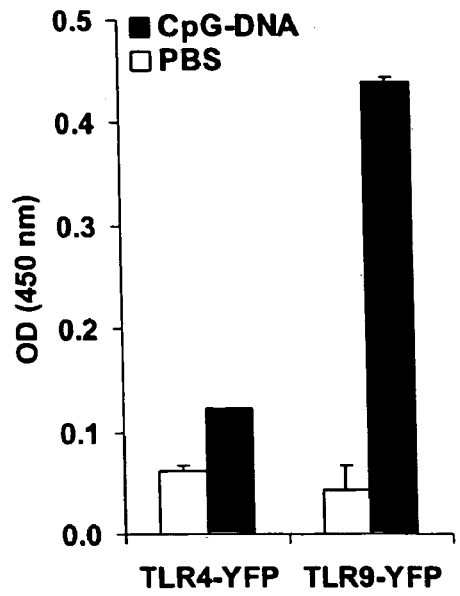
Fig. 4
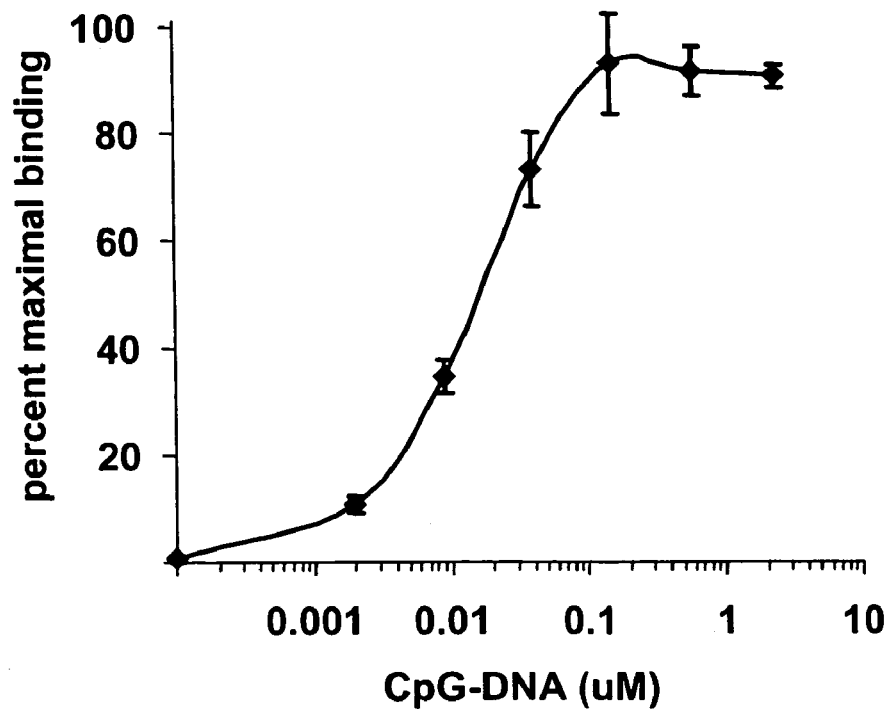

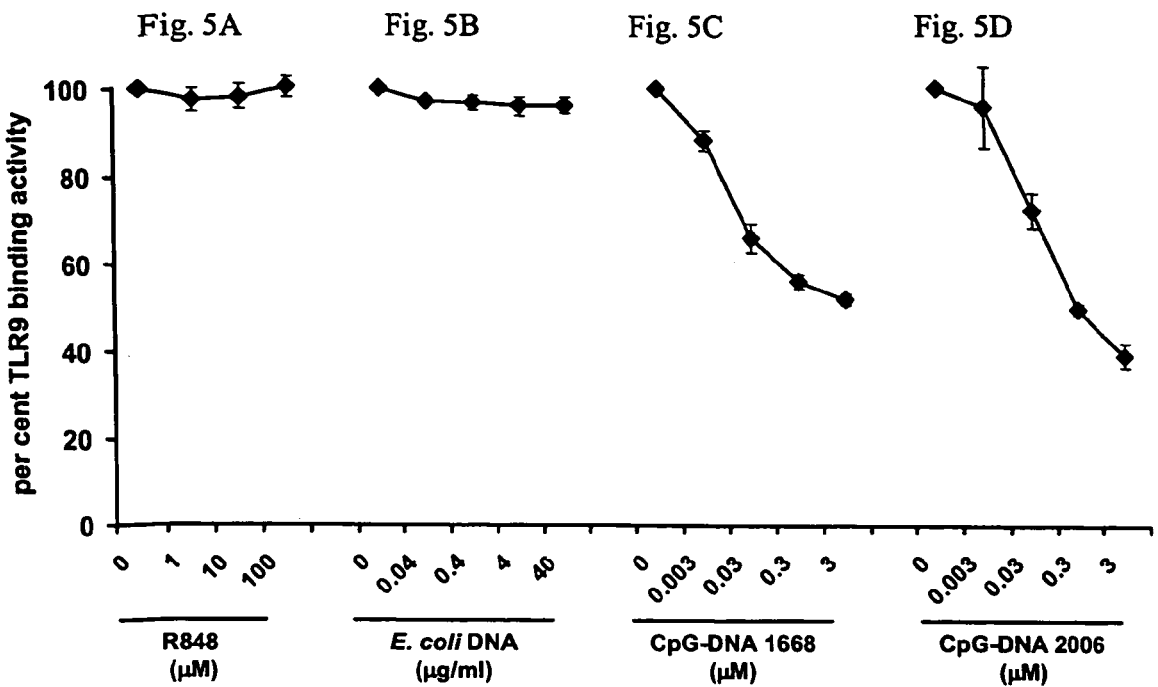
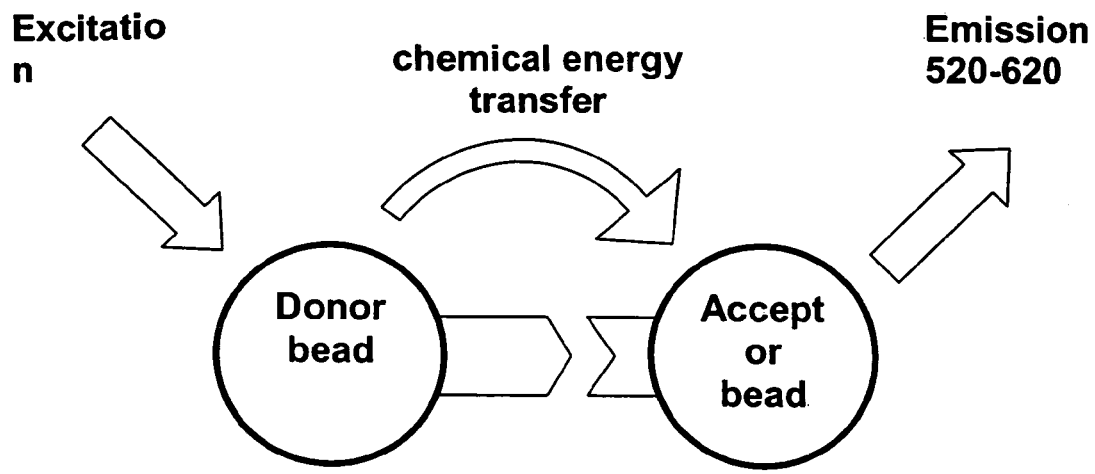

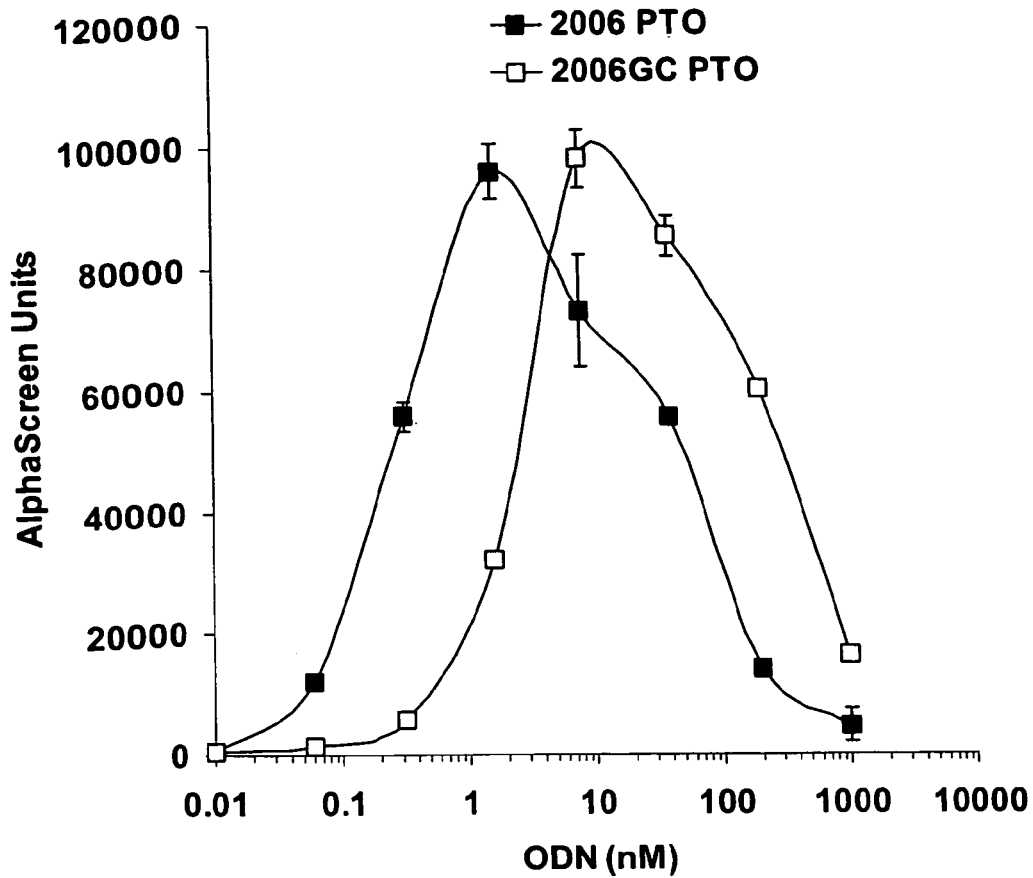
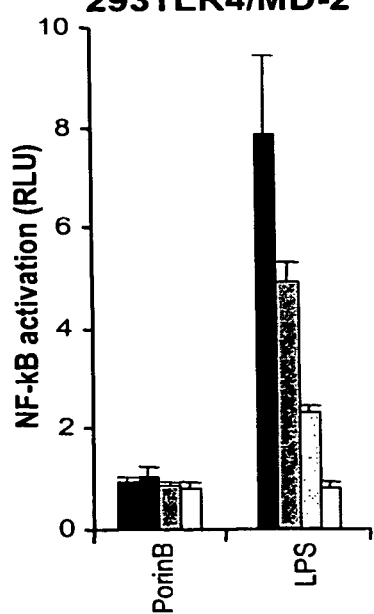
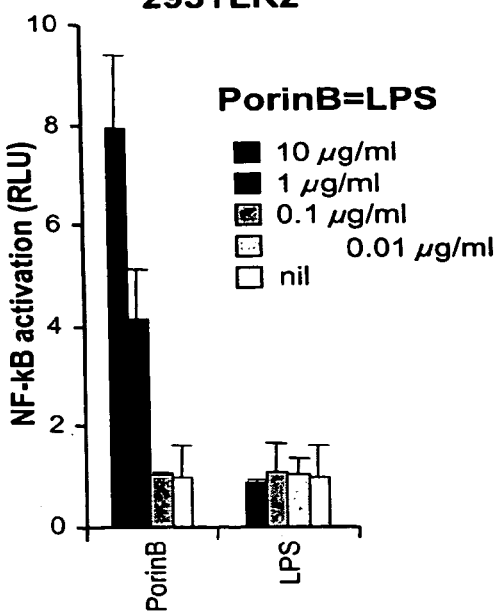

Fig. 7C
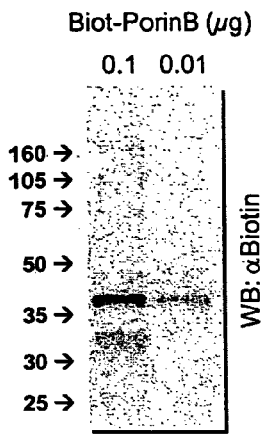
Fig. 7D
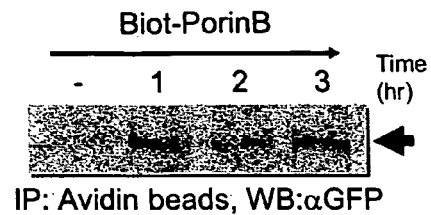
Fig. 8A
Fig. 8B
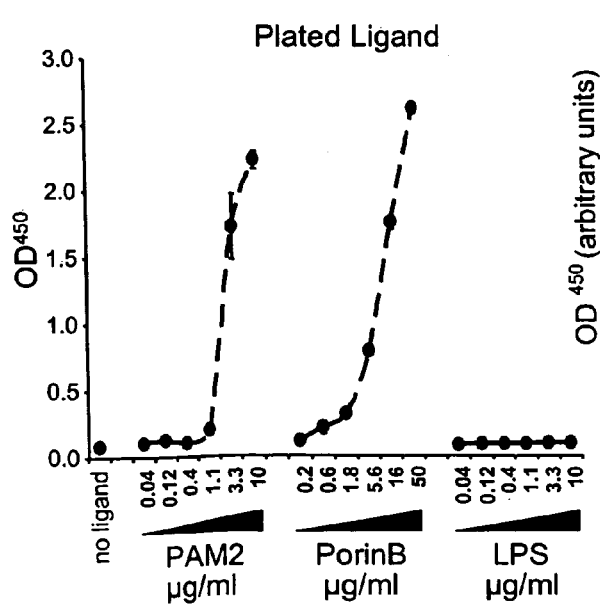
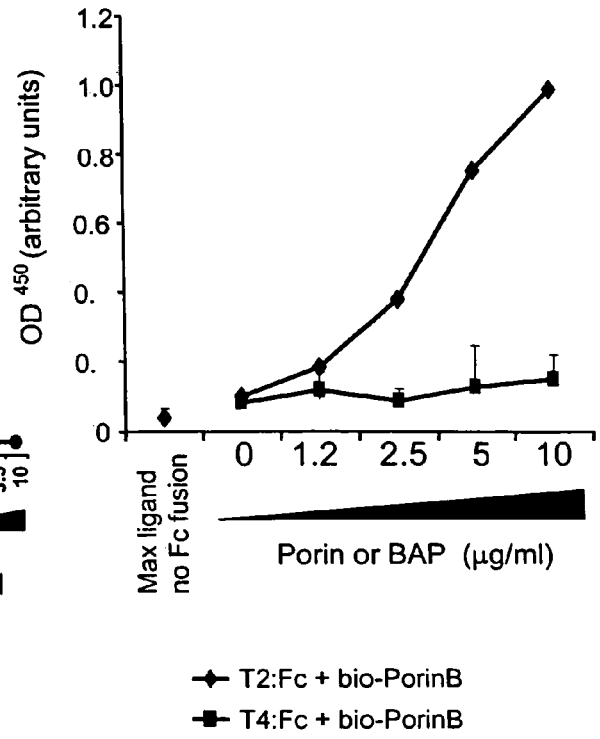

US 8,124,349 B2

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 1
tcgtcgtttt gtcgttttgt cgtt                                          24

<210> SEQ ID NO 2
<211> LENGTH: 31
<212> TYPE: DNA
<213> ORGANISM: Artificial Sequence
<220> FEATURE:
<223> OTHER INFORMATION: Primer

<400> SEQUENCE: 2
gaagcccctg cccggatcca tgggtttctg c                                  31
```

```
<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
tccggctcac tcgagttcgg ccgtgggtcc ctg                    33
```

TOLL-LIKE RECEPTOR ASSAYS

CLAIM OF PRIORITY

This application is a continuation of U.S. Utility patent application Ser. No. 11/014,351, filed Dec. 16, 2004 now abandoned, which claims priority under 35 USC §119(e) to U.S. Provisional Patent Application Ser. Nos. 60/530,115, and 60/530,699, both filed on Dec. 16, 2003, the entire contents of which are hereby incorporated by reference.

FEDERALLY SPONSORED RESEARCH OR DEVELOPMENT

The U.S. Government has certain rights in this invention pursuant to Grant No. GM54060 awarded by the National Institutes of Health.

TECHNICAL FIELD

This invention relates to methods of identifying and using modulators of Toll-like receptors.

BACKGROUND

Effective activation of the immune system in response to a pathogen depends on the ability of antigen presenting cells to deliver the necessary co-stimulatory ("danger") signal in the context of antigen presentation. In mammals, this "adjuvant" effect is the result of the triggering of a family of germline-encoded receptors (Toll-like receptors, TLRs), which recognize a variety of conserved microbial and endogenous molecular structures. Activation of different TLRs elicits a proinflammatory response, which promotes the elimination of the pathogen via the activation of the innate arm of the immune system as well as determining the type of adaptive immune response (Th1 versus Th2 responses). Skewing between cellular or humoral immune effector function largely depends on the nature of the pathogenic insult and therefore on the specific array of TLRs that is activated.

In rational vaccine design (for example, for infectious disease prevention or cancer immunotherapy), manipulation of TLR activation is a desirable approach to developing synthetic immune activators (adjuvants) that can promote an appropriate response (i.e., cellular versus humoral). Conversely, hyperactivation of TLRs may lead to pathological situations in which the blockage of the receptor is desirable, for example, in some endotoxin-related conditions in which MD-2/TLR4, the signaling receptor complex for Gram-negative lipopolysaccharide, is activated.

SUMMARY

The present invention is based, at least in part, on the discovery that mammalian TLRs, e.g., TLR9 and TLR2, interact directly, e.g., bind directly to, ligands, e.g., stimulatory pathogen-derived ligands such as lipopolysaccharide (LPS) and CpG DNA. The invention includes methods of screening for compounds that can act as TLR ligands, and for compounds that can modulate an interaction (e.g., binding) between a TLR polypeptide and a TLR ligand. Such compounds, referred to herein as "TLR interactors," can increase or decrease the interaction (e.g., binding) between a TLR and a TLR ligand. In general, such compounds can modulate TLR signaling, e.g., in a cell that has been activated for such signaling (e.g., by contacting the cell with a TLR ligand). These compounds can be used to modulate immune responses to pathogens.

Accordingly, the invention relates to methods of identifying Toll-like receptor (TLR) interactors. The methods include providing a sample comprising a TLR polypeptide; contacting the sample with a biotinylated test compound, thereby providing a test mixture; incubating the test mixture with a particle comprising a molecule that binds to biotin, e.g., a particle comprising avidin, streptavidin or NeutrAvidin™ (a deglycosylated form of avidin), e.g., a bead, under conditions and for a time sufficient to permit binding between the biotinylated test compound and the particle, thereby providing a bound particle; isolating the bound particle; and determining if the bound particle is associated with the TLR polypeptide. A bound particle that is associated with the TLR polypeptide indicates that the test compound is a Toll-like receptor (TLR) interactor. In some cases, the sample is a biological sample. The test mixture can include at least two different TLRs, which may or may not interact with each other.

The invention also relates to methods of identifying compounds that modulate the interaction between a Toll-like receptor (TLR) and its cognate TLR ligand. The methods include providing a sample comprising a TLR polypeptide; contacting the sample with a cognate TLR ligand and a test compound (consecutively, in either order, or simultaneously), thereby forming a test sample; incubating the test sample for a time and under conditions sufficient for the TLR ligand to bind to the TLR polypeptide in the absence of the test compound; and determining binding between the TLR polypeptide and the TLR ligand in the test sample, wherein a difference binding in the test sample compared to a control indicates that the test compound is a candidate compound for modulating TLR signaling. In some embodiments, the difference in binding is one or more of: a difference in a rate of binding; a rate of dissociation; a difference in an amount of binding; or a difference in an affinity of binding.

The method of claim 21, further comprising formulating a therapeutic composition comprising a candidate therapeutic compound and a pharmaceutically acceptable carrier.

In some embodiments, the TLR ligand or TLR polypeptide is biotinylated. In some embodiments, the TLR polypeptide is a chimeric polypeptide comprising a TLR protein or fragment thereof and a second protein, e.g., an Fc fragment, or a fluorescent protein, e.g., Green fluorescent protein (GFP) or a fluorescent variant thereof In some embodiments, the TLR ligand or TLR polypeptide is bound to a solid surface; e.g., either the TLR ligand or the TLR polypeptide is biotinylated and the solid surface comprises avidin, streptavidin, or NeutrAvidin™, a deglycosylated form of avidin.

In some embodiments, one or more of the TLR polypeptide and the TLR ligand is labeled, e.g., with a compound that is detectable with time resolved fluorimetry, e.g., a europium compound or an allophycocyanin compound.

In some embodiments, binding between the TLR polypeptide and the TLR ligand is detected using an antibody that specifically binds to the TLR polypeptide. In some embodiments, the TLR polypeptide is a chimeric polypeptide, and the antibody binds to the second protein in the chimeric polypeptide.

In some embodiments, the TLR polypeptide and TLR ligand are in solution. In some embodiments, time-resolved fluorimetry is used to detect the binding.

In some embodiments, the TLR polypeptide or TLR ligand is bound to an isolatable substrate, e.g., a bead.

In some embodiments, the TLR polypeptide is a TLR1, TLR2, TLR3, TLR4, TLR5, TLR6, TLR7, TLR8, TLR9, or TLR10 polypeptide. In some embodiments, the TLR polypeptide is TLR2 or TLR9.

In some embodiments, the methods further include determining whether the test compound modulates TLR9-mediated signaling. A test compound that has been screened by a method described herein and determined to modulate TLR9 signaling, can be considered a candidate compound. A candidate compound that has been screened, e.g., in an in vivo model of a disorder, e.g., a disorder associated with TLR9 signalling, e.g., inflammation, autoimmune disorders, and pathogen infection, and determined to have a desirable effect on the disorder, e.g., on one or more symptoms of the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions. The invention also relates to compounds that modulate TLR9 signalling, identified by a method described herein, and therapeutic compositions containing the compounds, as well as methods of treating disorders associated with TLR9 signalling by administering the compounds. Methods of preparing and administering such compounds are known in the art.

Thus, the invention includes methods of administering a compound that modulates Toll-like receptor (TLR) signaling, identified by a method described herein, to an animal model of a disorder associated with TLR signalling; and evaluating an effect of the compound on a parameter of the disorder in the animal, e.g., a symptom or other clinical parameter, e.g., morbidity, mortality, or time of onset. A positive effect of the compound indicates that the compound is a candidate therapeutic compound for the treatment of the disorder. The candidate therapeutic compound can be optimized, and formulated with a pharmaceutically acceptable carrier to make a therapeutic composition for the treatment of the disorder.

As used herein, a "TLR polypeptide" can include a full-length TLR polypeptide or a suitable fragment thereof, as described herein. In some embodiments, the TLR polypeptide is a chimeric protein, e.g., a peptide includes a second protein (e.g., a fluorescent polypeptide, a tag, or an Fc region of an antibody) expressed in frame with the TLR as a single molecule. The TLR ligand or TLR polypeptide can be bound to a solid surface (in one example, the TLR ligand is biotinylated and the solid surface comprises avidin, streptavidin, or NeutrAvidin™, a deglycosylated form of avidin). In another embodiment, the TLR ligand and/or TLR polypeptide is labeled, e.g., with a lanthanide chelate fluorophore, and time-resolved fluorimetry is used to detect the binding. In some embodiments, an antibody that specifically binds to the TLR polypeptide is used to detect binding between a TLR polypeptide and a TLR ligand; for example, an antibody that specifically binds to a chimeric TLR protein (e.g., to the non-TLR portion of the chimera) can be used to detect binding between the TLR polypeptide and TLR ligand. The antibody can be labeled, e.g., with a lanthanide chelate fluorophore, and time-resolved fluorimetry is used to detect the binding. The method can also be performed such that the TLR polypeptide and TLR ligand are in solution. In another embodiment, the TLR polypeptide and/or the TLR ligand is bound to a collectable substrate, e.g., a bead.

By "specifically binds" is meant a molecule that binds to a particular entity in a sample, e.g., a specific TLR protein, but which does not substantially recognize or bind to other molecules in the sample, e.g., another type of TLR polypeptide or a non-TLR protein.

"Polypeptide" means a chain of amino acids regardless of length or post-translational modifications, and thus includes proteins and peptides.

A "TLR-interactor" is a molecule (e.g., an organic or inorganic small molecule, peptide, polypeptide, or nucleic acid) that associates with, e.g., binds directly or indirectly to or forms a complex with, a TLR polypeptide, e.g., in a cell. TLR-interactors include molecules that co-immunoprecipitate with a specific TLR polypeptide, as well as molecules that specifically bind to the TLR polypeptide. TLR interactors can be of cellular origin or exogenously added, including naturally-occurring molecules and synthetic molecules. TLR interactors include TLR ligands and molecules that interfere with binding of a TLR polypeptide and TLR ligand, e.g., a naturally occurring TLR ligand such as a pathogen-derived ligand or analog thereof. Such molecules can be identified using methods described herein.

A "TLR ligand" is a molecule that interacts with a TLR by binding to the TLR, i.e., there is a direct association with the TLR. A "cognate" TLR ligand is a natural or artificial ligand that can bind to and activate signaling through a particular TLR or TLRs. For example, CpG-DNA is an example of a cognate ligand for, e.g., TLR7, TLR8, or TLR9. LPS is an example of a cognate ligand for TLR2. In general, the binding of a TLR polypeptide and a TLR ligand is non-covalent in nature. In some embodiments, a TLR ligand can activate or inhibit signaling through the TLR.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF DRAWINGS

FIG. 3A is a bar graph that depicts the results of experiments in which a solid phase assay was used to detect TLR4$^{YFP}$ or TLR9$^{YFP}$ binding to immobilized CpG-DNA or control (PBS). Bound TLR was detected with GFP antibody and HRP-conjugated mouse monoclonal antibody followed by a color reaction to detect HRP activity. Absorbance at 450 nm was detected.

FIG. 3B is a bar graph that depicts the results of experiments in which a solid phase assay was used to detect TLR4$^{YFP}$ or TLR9$^{YFP}$ binding to anti-GFP coated onto microtiter plates or control (PBS). Bound TLR was incubated with biotinylated ligand (CpG-DNA). The bound ligand was detected with HRP-conjugated streptavidin followed by a color reaction to detect HRP activity. Absorbance of the color obtained after adding HRP substrate was read at 450 nm.

FIG. 4 is a graph illustrating the results of experiments in which increasing amounts of biotinylated CpG-DNA (2006) were coated onto microtiter plates. Cellular lysates containing TLR9-Yellow Fluorescent Protein (TLR9$^{YFP}$) were incubated then detected by binding to anti-GFP monoclonal GFP and anti-mouse-HRP followed by a color reaction to detect HRP activity. Absorbance was measured at 450 nm. The results are expressed as the percent of half-maximal binding.

FIGS. 5A-D are graphs depicting the results of experiments showing the percent TLR9 binding activity to CpG-2006 immobilized on plates in the presence of different concentrations of various compounds in solution; R848, E. coli DNA, CpG-DNA 1668, and CpG-DNA 2006.

FIG. 6A is a schematic illustration of the principle behind the AlphaScreen™ assay.

FIG. 6B is a line graph showing the results of an AlphaScreen™ assay of the interaction of TLR9-Fc with CpG-DNA (2006 PTO filled squares) and GpC-DNA (2006 GC PTO, open squares).

FIGS. 7A and 7B are bar graphs illustrating the levels of NFκB activation in HEK 293 cells stably expressing either TLR4 and MD-2 (FIG. 7A) or TLR2 (FIG. 7B) after stimulation with PorinB in doses of 0.01 µg/ml (lightest gray bars), 0.1 µg/ml (medium gray bars), 1 µg/ml (dark gray bars), or 10 µg/ml (black bars).

FIG. 7C is a Western blot showing levels of biotinylated PorinB, probed with an anti-biotin antibody (α-biotin), demonstrating the purity of the preparation.

FIG. 7D is a Western blot showing levels of binding of PorinB to cell-surface TLR2$^{GFP}$ fusion constructs, detected using an anti-GFP antibody, at 0, 1, 2, and 3 hours after stimulation with biotinylated PorinB.

FIG. 8A is a line graph showing the binding of different concentrations of plated ligands to a TLR2:Fc fusion protein.

FIG. 8B is a line graph showing that increasing concentrations of Porin or bacterial alkaline phosphatase (BAP), bind to TLR2:Fc (filled diamonds), but not to TLR4:Fc (filled squares).

DETAILED DESCRIPTION

Figure 1A:
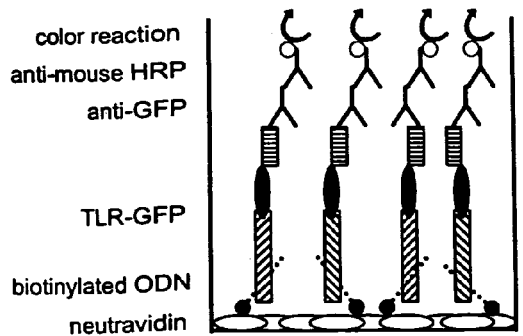
FIG. 1A is a schematic drawing of a ligand binding assay in which biotinylated ligand (biotinylated oligodeoxynucleotide; biotinylated ODN) is immobilized on NeutrAvidin™-coated microtiter plates. TLR-Green Fluorescent Protein (TLR$^{GFP}$) is bound to the biotinylated ligand and bound TLR is detected with an anti-GFP monoclonal antibody, which is detected using anti-mouse antibody conjugated to horseradish peroxidase (anti-mouse HRP) after a color reaction to detect peroxidase activity.

Toll-like receptors (TLRs) are molecules that can act as mediators of immune system responses and of related physiological phenomena such as inflammation. TLRs manifest their effects as part of a signaling pathway that leads to the expression and activation of molecules that ultimately induce, e.g., immune system activation. Accordingly, identification of molecules involved in TLR signaling pathways is useful for identifying targets for drugs that affect immune system activation and related effects. The identification of compounds that disrupt or enhance the interaction between TLR polypeptides and their cognate ligands or analogs thereof (e.g., molecules that are known to be capable of interacting with the TLR and can elicit at least one activity associated with signaling by that TLR, e.g., analogs of naturally-occurring ligands) is useful for identifying compounds that modulate the effects of TLR signaling, for example by reducing inflammation or decreasing or enhancing an immune response. Because of the importance of TLRs in immune response signaling, fast and inexpensive strategies for identifying compounds that are able to interact with TLRs are of commercial and practical use.

Several different approaches for screening assays suitable for the identification of TLR modulators that interact with TLRs (TLR interactors) are described herein. TLR interactors include molecules that directly bind to a TLR polypeptide (e.g., TLR ligands) or are associated with a TLR polypeptide in a complex that includes other proteins. The assays can be adapted to identify compounds that can disrupt the interaction between a TLR polypeptide and its cognate ligand.

Screening Assays

In general, the invention provides methods (also referred to as "screening assays") for identifying compounds that can modulate TLR signaling. Such compounds are candidate compounds (e.g., proteins, peptides, peptidomimetics, peptoids, small non-nucleic acid molecules, nucleic acids, synthetic nucleic acids, or other drugs) for the treatment of disorders associated with TLR signaling. The compounds can be, e.g., naturally occurring interactors (e.g., bacterial DNA) or synthetic molecules such as an engineered CpG-DNA. In general, the compounds will be agonists or antagonists of the interaction between a TLR polypeptide and its cognate TLR ligand. For example, some compounds may have competitive or non-competitive action for TLR ligands.

A number of methods are known in the art for determining the effect of a test compound on ligand/receptor interactions. For example, three commonly used experimental protocols to determined binding include:

(1) Saturation binding experiments. The extent of binding is measured in the presence of different concentrations of the a ligand. From an analysis of the relationship between binding and ligand concentration, the number of binding sites, $B_{max}$, and ligand affinity, $K_D$, can be determined.

(2) Kinetic experiments. In these experiments, saturation and competition experiments are allowed to incubate until binding has reached equilibrium. Kinetic experiments measure the time course of binding and dissociation to determine the rate constants for ligand binding and dissociation. Together, these values can be used to calculate $K_D$.

(3) Competitive binding experiments. The binding of a single concentration of ligand is measured in the presence of various concentrations of an unlabeled competitor. The data can be used to determine the affinity of the receptor for the competitor.

All of these methods are known in the art. See, e.g., Clegg, *Protein Targeting Protocols* (Methods in Molecular Biology, Vol 88), Humana Press (1998).

Compounds identified by a method described herein can have a stimulatory or inhibitory effect on the activity of a TLR, for example by stimulating or inhibiting TLR-mediated signaling (TLR signaling). For example, a compound may have a stimulatory or inhibitory effect on an activity of a TLR ligand, including the ability of the TLR ligand to stimulate TLR-mediated signaling. Thus, compounds identified using the methods described herein can be used to modulate the activity of TLR-mediated signaling. For example, a compound that increases the interaction between a TLR polypeptide and its cognate TLR ligand is useful for activating the immune system in a therapeutic or prophylactic protocol, or to elaborate a biological function of a TLR polypeptide and a TLR interactor, e.g., to identify new pathways for potential therapeutic modulation, e.g., new therapeutic targets. A compound that disrupts an interaction between a TLR polypeptide and a TLR interactor, e.g., a ligand, can be useful for decreasing an immune-mediated response such as an undesirable inflammatory response.

Determining the ability of a test compound to modulate TLR activity can be accomplished by monitoring, for example, any suitable aspect of signaling mediated by the particular TLR polypeptide, including activation of the immune system of a subject, e.g., a mammal, e.g., an experimental animal or a human, or activation of a cellular pathway associated with immune activation. Suitable methods include, but are not limited to, detecting cellular activation of TLR-expressing cells by measuring cytokine or chemokine responses, detection of surface upregulation of inducible genes (such as CD80, CD86, CD40, MHCII, or CD54), measuring the expression, activity, or translocation of DNA-binding or nuclear transcription factors (e.g., NF-κB), Northern blotting to detect the synthesis of immunologically relevant genes, RT-PCR or real-time PCR assays to detect upregulation of RNA encoding immunologically relevant genes (including genes of the signaling pathway activated by the TLR polypeptide, e.g., TNF-alpha, IFN-alpha, IL-6, IL-1, IL-8 and RANTES), activation of IL-10-producing regulatory T cells in response to TLR activation (e.g., van der Kleij et al., 2002, J. Biol. Chem., 277:48122-48129), detection of dendritic cell maturation as a readout of immune stimulation, or detection of B cell proliferation in response to ligand stimulation. Methods of detecting such activities are known in the art. In cell-based or cell-extract assays, the cell can be, for example, of mammalian origin, e.g., human, murine, rabbit, hamster, monkey, or rat. In general the cell is one that either naturally expresses the TLR polypeptide of interest or the cell is genetically engineered to express the TLR polypeptide of interest. Generally, upon stimulation with the appropriate molecule (e.g., a CpG-DNA for stimulation of TLR9 signaling), the cell is also capable of carrying out one or more activities in the signaling pathway of the TLR polypeptide of interest.

Toll-Like Receptor Ligand Binding Assays

In general, the new assays described herein for identifying compounds that interfere with the interaction between a TLR polypeptide and TLR ligand involve a known TLR cognate ligand that can bind to the TLR polypeptide used in the assay (e.g., any of TLRs 1, 2, 3, 4, 5, 6, 7, 8, 9 and/or 10), to a complex of a TLR polypeptide and an associated molecule (e.g., TLR4 and MD-2), or to a homo- or heteromultimeric complex of two or more TLRs (e.g., TLR2/TLR1 or TLR2/TLR6 heteromultimers). In some embodiments, the TLR ligand and/or TLR polypeptide is labeled. A test compound (e.g., a potential receptor agonist or antagonist) is included in a test sample and is examined for its ability to compete for the TLR ligand interaction with the TLR polypeptide. Because only the known ligand is labeled, a decrease in the amount of measured label indicates that the test compound interacted with the receptor or interacted with the ligand in a manner that inhibits interaction of the ligand with the TLR polypeptide. A test compound can also increase the binding of a TLR ligand, thereby lowering the $K_d$ for a ligand to the respective TLR polypeptide.

Assays for identifying compounds that interact with, e.g., bind directly or indirectly to or form complexes with, a TLR polypeptide are also described herein. Such assays generally involve labeling potential TLR interactors and contacting the TLR polypeptide with the labeled interactor(s) as described below. Molecules that are associated with the TLR polypeptide can then be identified using methods known to those in the art, including electrophoresis and sequencing.

In some assays, TLR interactors are identified, for example, by conducting an assay described herein in the presence of a biological sample suspected of containing a TLR interactor or in the presence of a mixture of library of molecules suspected of containing a compound that can interact with a TLR polypeptide. After a molecule is identified as interacting with a TLR polypeptide, characteristics of the TLR interactor can be determined. Such characteristics include, but are not limited to, the chemical nature of the interactor (e.g., a nucleic acid, a polypeptide, a small non-nucleic acid organic compound, or a small inorganic compound), the molecular weight of the compound, the charge of the compound (e.g., at physiological pH), and the ability of the compound to induce or inhibit activation of the cognate TLR polypeptide to with which it can interact). Methods known in the art can be used to optimize the interactor, e.g., to increase efficacy, binding, or other desirable attributes.

Precipitation Assays

One method of identifying compounds that modulate an interaction (e.g., binding) between a TLR polypeptide and a TLR ligand is a precipitation assay. In general, the TLR ligand (e.g., CpG-DNA or lipopolysaccharide (LPS)) is labeled using methods known in the art. For example, the TLR ligand can be biotinylated using methods known in the art, and incubated with a cell expressing the cognate TLR polypeptide. In some embodiments, after incubation under conditions and for a period of time sufficient to permit association of the TLR polypeptide and ligand (at least about 1 minute, e.g., 5 minutes, 10 minutes, 15 minutes, 30 minutes, 1 hour, 2 hours, 5 hours, 8 hours, 16 hours, or 24 hours), the cells are lysed and the biotinylated ligand is precipitated, e.g., using a collectable substrate that can bind to biotin, such as streptavidin-coated beads. Other biotin-binding entities can be used, e.g., avidin or NeutrAvidin™, a deglycosylated form of avidin. The precipitated material is electrophoresed, transferred to membranes and visualized on Western blots. Alternatively, TLR polypeptide/ligand interaction can be determined by incubating cellular lysates with labeled ligand and TLR polypeptide/ligand interaction is detected similarly. In some embodiments, instead of a biotin label, a different small molecule label such as digoxin is used. The collectable substrate is coated with a suitable molecule (e.g., an antibody or antibody fragment) that can bind to the small molecule label.

The amount of TLR polypeptide bound to the biotinylated ligand can be quantitated using methods known in the art. For example, if a TLR fusion protein (e.g., composed of a TLR polypeptide and a fluorescent protein), is used as the TLR polypeptide, the fluorescent protein can be detected using methods known in the art, e.g., by direct detection of the fluorescent protein, or in a sandwich assay in which an antibody that specifically binds to the fusion protein (e.g., to the fluorescent protein part of the fusion protein) is added to the precipitate and the antibody detected using a second antibody that specifically binds to the first antibody and is also conjugated to a detectable label such as horseradish peroxidase (HRP). This precipitation assay can provide a control or reference for assays testing the ability of a test compound to modulate the interaction between the TLR polypeptide and its ligand. In such assays, a test compound is included in the incubation mixture and the amount of interaction between the TLR polypeptide and ligand assayed. A comparison between the control and the sample containing the test compound is made (e.g., by assaying the amount of signal on the Western blot). A decrease in the amount of interaction in the presence of the test compound compared to the amount of interaction in the absence of the test compound indicates that the test compound decreases the interaction. Conversely, an increase in the amount of interaction between the TLR polypeptide and ligand in the presence of the test compound indicates that the test compound increases the interaction (e.g., by decreasing the Kd). An embodiment of the precipitation is described in the Examples (infra).

The precipitated material can also be subjected to further analysis to identify TLR interactors in the precipitate. For example, proteins in the precipitate can be separated by electrophoresis and proteins in bands can be sequenced. Molecules identified in this assay can serve as targets for compounds that affect TLR-mediated signaling and affect immune system activation and inflammation.

Assays will typically be carried out in vitro, e.g., using a cell lysate, or a cell fraction that contains a suitably labeled TLR polypeptide.

The assay described above can be modified for use with a ligand that is labeled with any entity that can be bound by a second entity that is bound to a bead or other collectable substrate. Collectable substrates can include substrates that are collectable by, e.g., centrifugation, floating, settling, magnetism, or filtration. For example, the ligand can be labeled with a tag that can be detected using immunocytochemical methods. In this case, the appropriate second entity that binds the tag is attached to the substrate and the assay carried out substantially as discussed above.

This type of assay, in which the ligand is labeled and detected, provides advantages over methods in which only the TLR polypeptide is labeled. For example, using this method, it is possible to determine the kinetics of the interaction between the TLR polypeptide and the TLR ligand. Also, it can be easier to label the ligand than to engineer a labeled, functional TLR polypeptide.

In some embodiments, the method is an assay that can be used to identify novel candidate TLR interactors, e.g., ligands. For example, a sample (e.g., a cell or cell lysate) containing a labeled (e.g., by biotinylation) test compound, e.g., a potential TLR ligand, is incubated with the TLR polypeptide. After incubation under conditions and for a period of time sufficient to permit association of the TLR polypeptide and a TLR ligand (at least about 1 minute, e.g., 5 minutes, 10 minutes, 15 minutes, 30 minutes, 1 hour, 2 hours, 5 hours, 8 hours, 16 hours, or 24 hours), the labeled test compound is precipitated, e.g., a biotinylated test compound (and any molecules bound to or complexed with it) is precipitated using streptavidin-coated beads. The precipitated material is transferred to a membrane and visualized on Western blots; test compounds that precipitate TLR polypeptide are candidate TLR interactors.

Solid Phase Assays

The use of solid phase binding assays has certain advantages over a ligand-precipitation approach. Depending on the experimental setup for a solid phase assay, either the ligand or the TLR polypeptide is immobilized, e.g., on microtiter plates, and binding of the receptor or the ligand to the immobilized entity is detected and measured. Handling of reagents can be automated and small volumes can be used to limit the amounts of reagents necessary to carry out the assay. Since multiple microtiter plates can be used in these assays, a large number of compounds can be tested simultaneously. Thus, this type of assay is useful for high-throughput drug screening purposes in which handling in a plate environment and a relatively large number of samples is advantageous.

FIGS. 1A-1D illustrate the general design of four exemplary solid phase receptor ligand assays. There are two general types of setups (ligand coating or receptor coating) and two types of detection systems described although other detection systems known in the art can be used. The first detection system employs enzyme-linked immunosorbent assay (ELISA) technology for detection and the second type of detection system uses a fluorescence-based detection technology.

In one example of a solid phase assay, biotinylated ligand (e.g., biotin-CpG-DNA) is immobilized on a microtiter plate that is coated with a molecule that binds biotin, e.g., avidin, NeutrAvidin™, streptavidin, or an anti-biotin antibody. The TLR polypeptide of interest is labeled and is incubated in the prepared plates. The TLR polypeptide can be purified, partially purified, or presented in a cell lysate. In general, the TLR polypeptide is labeled by virtue of it being a fusion protein, e.g., a TLR polypeptide with a fluorescent protein such as YFP, GFP, Red Fluorescent Protein (RFP) or CFP (Cyan Fluorescent Protein). Methods of making such fusion proteins and stable cell lines that produce such fusion proteins are known in the art (e.g., Latz et al., 2002, J. Biol. Chem. 277:47834-47843). TLR polypeptide bound to the immobilized ligand can be detected using a sandwich method. A primary antibody that specifically binds to the labeled TLR polypeptide (e.g., an antibody that binds to the fluorescent protein portion of the TLR fusion protein) is added to the plate, incubated, washed, and then a secondary antibody that can specifically bind to the primary anti-labeled TLR antibody, e.g., a secondary antibody that is conjugated to a detectable label, is applied. The detectable label can be enzymatic, e.g., horseradish peroxidase (HRP) or some other detectable label. FIG. 1A illustrates an assay of this type. Variations of this method can be used, such as the direct use of conjugated primary antibody or ProteinA/G-conjugated to HRP as secondary reagents, or secondary reagents conjugated with different enzymes (such as alkaline phosphatase) or fluorophores (such as Alexa™ 488).

Figure 1B:
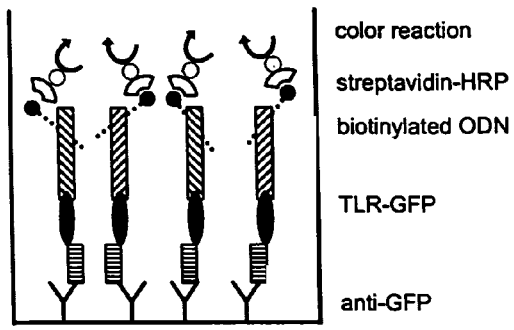
FIG. 1B is a schematic drawing of a ligand binding assay in which immobilized anti-GFP antibody (anti-GFP) captures TLR$^{GFP}$ (e.g., from a cellular lysate) and biotinylated ligand (biotinylated ODN) is bound to streptavidin conjugated to HRP after a color reaction to detect peroxidase activity.
Figure 1C:
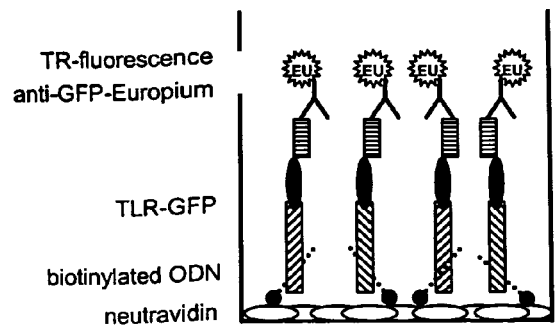
FIG. 1C is a schematic drawing of a ligand binding assay in which biotinylated ligand (biotinylated ODN) is immobilized on NeutrAvidin™-coated microtiter plates. TLR$^{GFP}$ is bound to the biotinylated ligand and bound TLR is detected with an anti-GFP monoclonal antibody that is also tagged with europium, which is detected using an acceptor in an assay to detect time resolved fluorescence (TR-fluorescence).
Figure 1D:
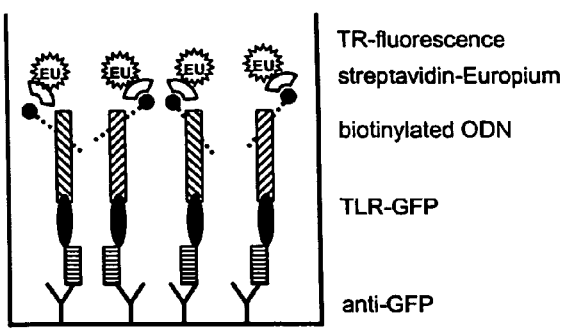
FIG. 1D is a schematic drawing of ligand binding assays in which immobilized anti-GFP antibody (anti-GFP) captures TLR$^{GFP}$ (e.g., from a cellular lysate) and biotinylated ligand (biotinylated ODN), which binds to streptavidin that is tagged with europium, which is detected using an acceptor in an assay to detect TR-fluorescence.

FIG. 1B illustrates an inverse assay in which the receptor (TLR) is captured on the plate via its tag (e.g., anti-GFP). Bound labeled, e.g., biotinylated, ligand can be detected, e.g., by the use of HRP-conjugated streptavidin in an enzyme-linked immunosorbant assay (ELISA). In both cases, a color reaction is obtained after adding substrate for the enzyme HRP. The receptor/ligand interaction is quantifiable by reading absorbance in a plate reader.

Other methods of detection can be used in solid phase assays. For example, time-resolved fluorescence (TR fluorescence) methods can be used. These methods use lanthanide chelate fluorophores. This method provides enhanced sensitivity and increased measurement range over standard ELISA methods. Time-resolved fluorimetry is possible when a fluorescent dye has a long decay time. This allows the measurement of emission after a time lag (up to 1 millisecond) when non-specific fluorescence from the sample and potential drug or microtiter plate has decayed. The elimination of interfering background contributes to higher sensitivity compared to methods using conventional fluorophores such as fluorescein and rhodamine. This assay is versatile in drug screening, since background fluorescence of the tested drug can be eliminated as a confounding factor due to the favorable fluorescence characteristics of the lanthanide chelate fluorophores.

A solid phase assay using lanthanide chelate fluorophores is similar to the ELISA-based assay described above. The steps of this assay involve the binding of receptor (FIG. 1C) or ligand (FIG. 1D) to the plate, incubating the immobilized entity with ligand or receptor and detecting the receptor-ligand interaction with europium-labeled detection reagent (e.g., europium-anti-GFP or europium-streptavidin). Such reagents are commercially available or can be prepared using commercially available kits (for example, DELFIA® products, PerkinElmer, Boston, Mass.). Once the europium-labeled reagents are bound, an enhancement step is applied to develop the fluorescence, which is then measured.

Homogeneous Assay

An alternative to the precipitation assay and the solid-phase ligand binding assays is a homogenous assay that has the advantage of further reduction of incubation times and wash steps. The homogeneous assay provides advantages in that it does not require washing steps, thus greatly simplifying the handling of the samples as compared to the precipitation and plate assay methods. In homogenous assays, all of the assay components remain in the same liquid phase. Homogeneous assays particularly benefit from the use of time-resolved fluorometry (TR fluorimetry) because the sample constituents present during detection can cause high background fluorescence when conventional fluorochromes are used.

Generally, in homogenous assays, the test compounds that are assayed for their ability to interact with a specified TLR polypeptide are combined in a sample mixture along with detection reagents. For example, when time-resolved (TR) fluorimetry is used (described in greater detail below), the TLR polypeptide is labeled with a fluorochrome suitable for use in TR fluorimetry. The detection reagents include an antibody, which can specifically bind the TLR polypeptide, labeled with the donor fluorochrome and a ligand bearing an acceptor fluorochrome that is compatible for use with the TLR polypeptide-associated fluorochrome in TR fluorimetry. Since the method is based on the detection of the fluorescence emitted only when the donor and the acceptor are in close proximity (e.g., by fluorescent resonance energy transfer (FRET)), free excess unbound reagents (e.g., those not in close proximity) do not contribute to the detected emitted light. Therefore, there is no need to wash out excess reagents.

In some embodiments, a test compound is assayed for its ability to enhance or decrease the interaction (e.g., binding) between a TLR polypeptide and one of its known ligands. In this case, the test compound is added to the incubation mixture containing the labeled TLR polypeptide and labeled TLR ligand. The amount of interaction between the TLR polypeptide and its ligand is measured in the presence and absence of the test compound. A decrease in the amount of interaction in the presence of the test compound indicates that the test compound decreases the interaction between the TLR polypeptide and its ligand and thus is a candidate compound for decreasing signaling by that TLR polypeptide. An increase in the amount of interaction between the TLR polypeptide and its interactor in the presence of the test compound indicates that the test compound is a candidate compound for increasing signaling by the TLR polypeptide. In some cases, compounds that disrupt the interaction between a TLR polypeptide and TLR ligand are further assayed for their ability to activate TLR signaling (i.e., to determine whether the compound is an agonist or antagonist of TLR signaling).

TR Fluorimetry

A sensitive and reliable labeling and detection system is based on TR-fluorimetry. As described herein, the method uses lanthanide chelates which give intense and long-lived fluorescence emission (greater than 1,000 µs), thereby enabling the measurement of fluorescence emission significantly later than excitation.

Figure 2:
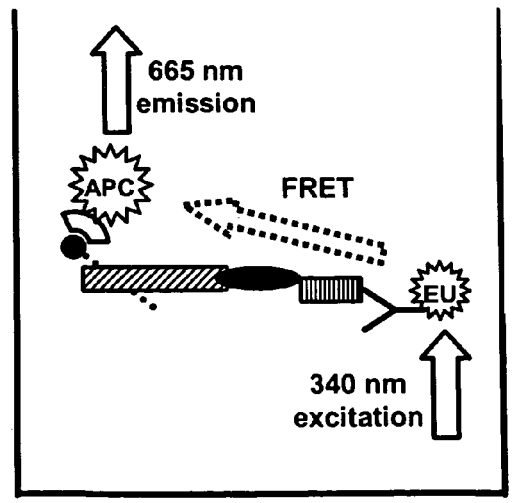
FIG. 2 is a schematic drawing depicting the principle of the homogenous ligand binding assay employing TR-fluorescent resonance energy transfer (e.g., LANCE™ technology). EU is europium, FRET is fluorescence resonance energy transfer, and APC is allophycocyanin.

TR fluorimetry can be used to assay molecules in the assays described herein. As discussed above, this method employs TR-FRET (time-resolved FRET) methodology (FIG. 2), based on labeling using lanthanide chelation. Lanthanide probes are used and their fluorescence lifetimes are assayed using a time-resolved fluorimeter. Lanthanide fluorophores can increase the sensitivity of an assay since the lanthanide fluorophores have a relatively long life span. Therefore, emissions can be measured after background fluorescence (e.g., from buffers and microtiter plates) has faded. In addition, different lanthanide probes exhibit a characteristic emission peak at specific wavelengths, which enhances the sensitivity of assays performed with this system. Since the peaks can be distinguished from one another, assays can be performed using more than one label. For example, a cell that stably expresses two different TLRs, each labeled with a different lanthanide fluorophore can be used, in the assays described herein. One TLR polypeptide can serve as a control. Alternatively, the method can be used to test compounds on more than one TLR at a time, thus increasing the efficiency of screens for molecules that interfere with TLR binding to its ligand. The lanthanide fluorophore, europium (Eu) is excited at 340 nm and due to a large Stokes shift, europium emits light at around 630 nm. In these assays, if the ligand and receptor are in close proximity (e.g., bound to each other), fluorescence energy transfer between the donor (europium) and the acceptor (allophycocyanin (APC)) is observed and emission of APC can be detected.

In the present methods, TR-FRET can be used by labeling the TLR of interest with a donor label such as europium chelate, and a ligand of the TLR is labeled with an acceptor label such as allophycocyanin (APC). Test compounds are assayed in the method for their ability to disrupt the interaction between the TLR and its ligand as measured by a decrease in energy transfer between the donor and acceptor molecules.

Commercially available methods of performing TR-FRET are available and can be adapted for use in the methods described herein, for example, the DELFIA® (PerkinElmer, Boston, Mass.) system for plate assays using TR-fluorimetry probes can be used. Reagents and kits for labeling compounds for use in such methods are available (e.g., LANCE™ and DELFIA™, PerkinElmer, Boston, Mass.). It should be noted that TR-FRET can be used in any of the screening assays described herein.

Amplified Luminescent Proximity Homogenous Assay (ALPHA)

In some embodiments, the methods include the use of the AlphaScreen™ Amplified Luminescent Proximity Homogeneous Assay (ALPHA) assays and reagents (PerkinElmer, Boston, Mass.), a bead-based assay system that provides very sensitive non-radioactive homogeneous assay technology for screening of biological interactions and activities. The assay, illustrated in FIG. 6A, employs two kind of beads, a donor and an acceptor bead. Typically, the ligand is immobilized on one bead and the receptor is immobilized on the other bead. The donor bead contains the photosensitizer phthalocyanine which can covert oxygen to a singlet oxygen after illumination of 680 nm light. The half-time of the lifetime of singlet oxygen is around 4 µsec, during which the molecule diffuses around 200 nm. If an acceptor bead is within a distance of less than 200 nm to the donor bead, energy is transferred to a thioxene derivative in the acceptor bead. This leads to the production of light in the range of 520-620 nm.

TLR Interactors and Ligands

In general, any TLR ligand can be utilized in the assays described herein. When TR fluorimetry methods are used, the ligand must be close enough to the TLR polypeptide for the energy transfer between the labeled TLR and TLR interactor to occur, e.g., bound directly to the TLR). Generally, known TLR ligands are used in the methods described herein. Such molecules include ligands comprising a pathogen-associated molecular pattern (PAMP) derived from a pathogen, e.g., microorganisms (e.g., bacterial lipopolysaccharide, lipoproteins, peptidoglycans, bacterial or viral DNA or RNA) or parasites (e.g., GPI-anchors, schistosomal lysophosphatidylserine). In some embodiments, the invention includes the use of other TLR activating agents such as synthetic compounds (e.g., DNA, RNA, synthetic lipopeptides) or TLR-interacting drugs (e.g., amphotericin, resiquimod, imiquimod) and endogenous TLR interacting molecules (e.g., heat-shock proteins).

TLRs and Cell Lines

Toll-like receptors (TLRs) are a family of type I integral membrane glycoproteins. All of the family members are characterized by the presence of two regions of leucine rich repeats (LRR)-containing in the N-terminal ("extracellular") domain and a toll interleukin 1 resistance (TIR) domain in the intracellular portion (see, e.g., Bell et al., 2003, Trends Immunol., 24(10):528-33).

At least ten different TLRs have been identified (Takeda et al., 2003, Ann. Rev. Immunol., 21:335-376. Epub Dec. 19, 2001; Barton and Medzhitov, 2002, Curr. Top. Microbiol. Immunol., 270:81-92). Any TLR polypeptide can be used in the assays described herein, provided that a method of producing the TLR polypeptide is available. In general, TLR nucleic acid sequences are known, and can be cloned and expressed using methods known in the art. Suitable toll-like receptors include, but are not limited to, toll-like receptor 1, *Homo sapiens* (GeneID: 7096; UniGene Cluster Hs.111805; NCBI Accession #NP_003254.2, AAC34137.1); toll-like receptor 2, *Homo sapiens* (GeneID: 7097; UniGene Cluster Hs.519033; NCBI Accession #AAH33756.1, AAM23001.1, AAC34133.1); toll-like receptor 3, *Homo sapiens* (GeneID: 7098; UniGene Cluster Hs.29499; NCBI Accession # AAC34134.1, NP_003256.1); toll-like receptor 4, *Homo sapiens* (GeneID: 7099 (var. C); UniGene Cluster Hs.174312; NCBI Accession #AAC34135.1, AAF89753.1, AAF07823.1, AAF05316.1); toll-like receptor 5, *Homo sapiens* (GeneID: 7100; UniGene Cluster Hs.114408; NCBI Accession #AAC34136.1, BAB43955.1); toll-like receptor 6, *Homo sapiens* (GeneID: 10333; UniGene Cluster Hs.366986; NCBI Accession #NP_006059.2, BAA78631.1); toll-like receptor 7, *Homo sapiens* (GeneID: 51284; UniGene Cluster Hs.179152; NCBI Accession # AAF60188.1, AAF78035.1, NP_057646.1, AAH33651.1); toll-like receptor 8, *Homo sapiens* (GeneID: 51311; UniGene Cluster Hs.272410 ; NCBI Accession #AAF64061.1, AAF78036.1); toll-like receptor 9 *Homo sapiens* (GeneID: 54106; UniGene Cluster Hs.87968; NCBI Accession # AAG01734.1, AAG01735.1, AAG01736.1, BAB19259.1); toll-like receptor 10, *Homo sapiens* (GeneID: 81793; UniGene Cluster Hs.120551; NCBI Accession #AAK26744.1, NP_112218.1); toll-like receptor 1, *Mus musculus* (GeneID: 21897; UniGene Cluster Mm.273024; NCBI Accession # AAG35062.1, AAG37302.1, NP_109607.1); toll-like receptor 2, *Mus musculus* (GeneID: 24088; UniGene Cluster Mm.87596; NCBI Accession #AAD46481.1, AAF04277.1, AAD49335.1, NP_036035.2, AAF28345.1); toll-like receptor 3, *Mus musculus* (GeneID: 142980; UniGene Cluster Mm.33874; NCBI Accession #AAK26117.1, AAL27007.1, NP_569054.2); toll-like receptor 4, *Mus musculus* (GeneID: 21898; UniGene Cluster Mm.38049; NCBI Accession # AAD29272.1, AAF04278.1, AAF05317.1, NP_067272.1, AAH29856.1); toll-like receptor 5, *Mus musculus* (GeneID: 53791; UniGene Cluster Mm.116894, Mm.347908; NCBI Accession #AAF65625.1, NP_058624.1); toll-like receptor 6, *Mus musculus* (GeneID: 21899; UniGene Cluster Mm.42146, Mm.347552; NCBI Accession #BAA78632.1, AAG38563.1, NP_035734.1); toll-like receptor 7, *Mus musculus* (GeneID: 170743; UniGene Cluster Mm.23979; NCBI Accession #AAK62676.1, NP_573474.1, AAL73191.1, AAL73192.1); toll-like receptor 8, *Mus musculus* (GeneID: 170744; UniGene Cluster Mm.196676; NCBI Accession # NP_573475.1, AAK62677.1); and toll-like receptor 9, *Mus musculus* (GeneID: 81897; UniGene Cluster Mm.44889; NCBI Accession #BAB19260.1, AAK29625.1, AAK28488.1, NP_112455.1); and homologs thereof. In some embodiments, the TLR is TLR2 or TLR9.

In addition, methods of engineering a TLR fusion protein (e.g., with a fluorescent protein) suitable for use in the assays are within the scope of the art (e.g., Latz et al., 2002, supra). As described herein, TLR-fluorescent protein fusion proteins can be engineered to enable tracking the TLR by virtue of the molecular tag in a variety of experimental systems. TLR-Fc fusion proteins can also be used, see U.S. Provisional Patent Application Ser. No. 60/598,774, filed Aug. 4, 2004, the disclosure of which is incorporated by reference herein. Stable cell lines have been established using such methods (e.g., Latz et al., 2002, supra). The stable cell lines have the common characteristic of stably expressing a chimeric fluorescent TLR. In general, the chimeric fluorescent TLR can, upon stimulation of the cell by a molecule known to activate the signaling pathway of the naturally occurring cognate of the chimeric TLR, induce one or more activities of the signaling pathway.

In some cases, TLRs recognize their cognate ligands by forming oligomeric complexes with other members of the family. This appears to be the case for TLR2, which requires cooperation with TLR1 or TLR6 in order to recognize certain ligands, e.g., Pam3CysK4 or Pam2CysK4, respectively. In such cases, both TLRs that are present in the heteromeric complex are used in the assay. For example, both TLRs that are naturally found in a heterodimer are coated onto an assay plate or are used in solution. If both are to be coated onto a prepared plate (e.g., a plate pre-coated with an antibody), then both TLRs are labeled with an attachment moiety (tag), e.g., hemagglutinin, biotion, GFP. In assays in which more than one TLR is being used and the TLRs are present in a liquid phase (e.g., for presentation in a plate assay in which the plate contains immobilized TLR ligand), the TLRs are provided in solution in approximately equal amounts or equal amounts of cell lysates from cells that express each TLR are used. One or both TLRs can be labeled (e.g., expressed as fusion proteins with a fluorescent protein) for subsequent detection steps.

Compounds

The test compounds used in screening assays can be obtained from any sources known in the art including any of the numerous approaches in combinatorial library methods known in the art such as biological libraries; peptoid libraries (libraries of molecules having the functionalities of peptides, but with a novel, non-peptide backbone which are resistant to enzymatic degradation but which nevertheless remain bioactive (e.g., Zuckermann et al., 1994, J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al. (1993, Proc. Natl. Acad. Sci. U.S.A. 90:6909), Erb et al. (1994, Proc. Natl. Acad. Sci. USA 91:11422), Zuckermann et al. (1994, J. Med. Chem. 37:2678), Cho et al. (1993, Science 261:1303), Carrell et al. (1994, Angew. Chem. Int. Ed. Engl. 33:2059), Carell et al. (1994, Angew. Chem. Int. Ed. Engl. 33:2061), and in Gallop et al. (1994, J. Med. Chem. 37:1233).

Libraries of compounds (or individual compounds or pools of compounds) can be presented as is appropriate for a particular assay. In general, compounds are presented in solution (e.g., Houghten, 1992, Biotechniques 13:412-421), or on beads (Lam, 1991, Nature 354:82-84). Libraries can also be presented on chips (Fodor, 1993, Nature 364:555-556), bacteria (Ladner, U.S. Pat. No. 5,223,409), spores (Ladner, U.S. Pat. No. 5,223,409), plasmids (Cull et al., 1992, Proc. Natl. Acad. Sci. USA 89:1865-1869) or on phage (Scott and Smith, 1990, Science 249:386-390; Devlin, 1990, Science 249:404-406; Cwirla et al., 1990, Proc. Natl. Acad. Sci. USA 87:6378-6382; Felici, 1991, J. Mol. Biol. 222:301-310; Ladner, supra).

Biotinylation

In some cases molecules are biotinylated for use in the assays described herein. Methods known in the art can be used. For example, ligands that contain primary amine-groups can be biotinylated in a one-step procedure using commercially available reagents. Lipopolysaccharides can be labeled with biotin in a two-step procedure as described in the art (e.g., Visintin et al., 2003, J. Biol. Chem. Online reference 10.1074/jbc.M306802200, September 5). Synthetic compounds can be synthesized with biotin (e.g., biotinylated CpG-DNA or biotinylated Pam3CysK4).

Correlating Information

The invention also relates to methods for correlating information about a test compound. Correlating means showing a relationship between a test compound and modulation of the interaction between a TLR polypeptide and a TLR ligand, to identify the compound as a compound that can modulate immune system activity. The correlating step can include, e.g., generating or providing a record, e.g., a printed computer-readable record, such as a laboratory record, electronic mail, or dataset, including information regarding a plurality of test compounds and their ability to modulate an interaction (e.g., binding) between a TLR polypeptide and a TLR ligand. The record can also include information about whether the test compound can, e.g., modulate TLR activity, and/or modulate immune system activity. The record can include other information, such as a specific test compound identifier, a date, an operator of the method, and/or information about the source, structure, method of purification or biological activity of the test compound. The record or information derived from the record can be used, e.g., to identify the test compound as a compound or candidate compound (e.g., a lead compound) for pharmaceutical or therapeutic use. The identified compound can be identified as an agent or a potential agent for treatment of diabetic nephropathy. Agents, e.g., compounds, identified by this method can be used, e.g., in the treatment (or development of treatments) for immune system related disorders or for increasing the activity of the immune system (e.g., as adjuvants for vaccine administration).

Uses

The methods and reagents described herein can be used in automated screening of large compound libraries to identify compounds that can interact with a TLR (e.g., TLR9). Compounds that bind to the TLR generally have the ability to either displace binding of a TLR interactor (e.g., ligand such as CpG-DNA) when the TLR interactor is bound to the TLR. In other embodiments, the compound, when immobilized (e.g., in a microtiter well) will directly bind the TLR. Once a compound is identified that can interact with the selected TLR, the compound can be characterized for function (e.g., agonistic, antagonistic, competitive, or cooperative activity). The compounds can be further tested for their ability to modulate TLR signaling, for example, by assaying the ability of the compound to modulate one or more indicia of activation of TLR signaling by the selected TLR. For example, expression of an RNA or protein, or an enzymatic activity known to be induced as part of the signaling of the selected TLR, (e.g., activation of NF-κB). Compounds can also be tested for their suitability for treating a subject in need of treatment.

The solid phase assay can be used to characterize the thermodynamic constants of the interaction of TLRs and their ligands. For example a TLR and a nucleic acid or nucleic acid analog. This information is useful for assessing the pharmacokinetic potential of the compound.

Compounds that stimulate or enhance TLR signaling are useful, for example, as immunostimulants. Immunostimulants can be useful for treating subjects who are immunocompromised or as adjuvants for increasing the response to a vaccine. Compounds that inhibit TLR signaling are useful, for example, as inhibitors of undesirable inflammatory responses or to inhibit an undesirable immune response as in certain inflammatory diseases such as rheumatoid arthritis or systemic lupus erythematosus.

Pharmaceutical Compositions and Methods of Administration

The therapeutic compounds described herein can be incorporated into pharmaceutical compositions. Such compositions typically include the nucleic acid molecule and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens;

antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The therapeutic compounds can also be prepared in the form of suppositories (e.g., with conventional suppository bases such as cocoa butter and other glycerides) or retention enemas for rectal delivery.

Therapeutic compounds comprising nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The pharmaceutical compositions can be included in a container, pack, or dispenser together with instructions for administration.

EXAMPLES

The following examples illustrate certain embodiments of the methods but are not to be construed as limiting.
Materials Reagents. Monoclonal antibody and polyclonal antiserum against GFP were obtained from Clontech (Palo Alto, Calif.) and Molecular Probes (Eugene, Oreg.), respectively. The HRP-conjugated polyclonal anti-biotin antibody was from New England Biolabs (Beverly, Mass.). Unless otherwise stated, other reagents were purchased from Sigma. Phosphothioate CpG-DNA was from MWG Biotech (High Point, N.C.). DNA was labeled at the 3-prime end with either fluorescent tags or biotin. The sequences of stimulatory CpG-DNA were as described in Bauer et al. (2001, Proc. Natl. Acad. Sci. USA 98:9237-9242). R848 is a commercially available (e.g., InvivoGen, San Diego, Calif.) and is an imidazoquinoline compound that stimulates activation of immune cells via TLR7/TLR8 pathways. CpG1668 is as described in Sparwasser et al. (1997, Nature 386:336-337).

Cellular Activation Assays—Dual Luciferase Reporter Assays for NF-κB Activation

Cellular activation was assessed by NF-κB-luciferase reporter assay. Briefly, HEK293 cells that stably express a TLR$^{FP}$ or empty vector (pcDNA) were seeded into 96-well tissue culture plates at a density of $2 \times 10^4$ cells/well. The following day, cells were transiently transfected with luciferase reporter genes using Genejuice (Novagen) per the manufacturer's recommendations. In order to assess NF-κB activation, an NF-κB-luciferase reporter gene consisting of an artificial promoter composed of a multimer of five NF-κB sites driving the firefly luciferase gene, was co-transfected with a constitutively active Renilla-luciferase reporter gene (Promega, Madison, Wis.).

Ligand-binding studies. Monolayers of cells expressing chimeric TLRs were incubated for 8 hours with 5 µM biotinylated CpG-DNA before lysis (Latz et al., 2002, supra) and microcentrifugation to remove nuclear debris. Alternatively, clarified cellular lysates were incubated with 5 µM biotinylated CpG-DNA. Streptavidin-coated beads (Sigma) (25 µl of a 50% suspension) were added to 500 µl of lysate and rotated for one hour at 4° C. In a parallel experiment, lysates were incubated with anti-GFP polyclonal antibody and 40 µl of packed protein A-Sepharose™ at 4° C. for one hour to assess overall protein levels of the chimeric TLRs. Pellets were washed four times in lysis buffer, resolved by SDS-PAGE, and transferred to nitrocellulose membranes (HyBond C, Amersham Biosciences). Membranes were blocked in 5% powdered milk (Gibco) and blotted with anti-GFP monoclonal antibody. Blots were then incubated with HRP-conjugated anti-mouse antibody and developed on Hyperfilm™ with the enhanced chemiluminescence HRP substrate system (Amersham Biosciences).

Example 1

TLR Plate Assay

Plate or solid phase assays are useful for identifying compounds that can modulate the interaction between a TLR and a TLR ligand. To demonstrate the principle of such plate assays, microtiter plates were coated with 0.3 µM biotinylated CpG-DNA (phosphothioate-stabilized CpG oligodeoxynucleotides, 2006; TCGTCGTTTTGTCGTTTTGTCGTT (SEQ ID NO:1) in PBS, and washed with PBS/0.05% Tween 20. Plates were generally freshly prepared but optionally can be stored before use. Control wells in the plates were only processed as for coating using phosphate buffered saline (PBS).

Fluorescent DNA constructs. TLR2$^{YFP}$ and TLR4$^{YFP}$ constructs were as described in Latz et al. (2002, J. Biol. Chem. 277:47834-47843). PCR of TLR9 was performed to construct chimeric fluorescent cDNAs. The primers for TLR9 were: 5'-GAAGCCCCTGCCCGGATCCATGGGTTTCTGC-3' (SEQ ID NO:2) and 5'-TCCGGCTCACTCGAGTTCGGC-CGTGGGTCCCTG-3'(SEQ ID NO:3). PCR fragments were cloned into the BamHI and XhoI sites of pcDNA3-CFP, pcDNA3-YFP and pcDNA3-GFP (Latz et al., 2002, supra). Retroviral constructs containing TLR9$^{YFP}$ and MyD88$^{CFP}$ were constructed similarly; PCR products were cloned into peak 12 mmp.

For the assay, the plates were incubated with cellular lysates (prepared as described above) from TLR9$^{YFP}$ or TLR4$^{YFP}$ (as a control for specificity) expressing HEK cells for one hour at room temperature. The plates were then washed and incubated with 0.5 µg/ml of a monoclonal anti-GFP antibody (Molecular Probes, Inc.) for one hour at room temperature. The plates were washed three times with PBS/Tween 20 0.05% at room temperature and the bound antibody was detected by incubating with an anti-mouse IgG conjugated to horseradish peroxidase (HRP) for one hour at room temperature. The plates were developed by adding HRP-substrate and the color development was quantified by absorbance measurements at 450 nm after stopping the reaction by addition of 2 N NaHCO$_3$ to bring the concentration to 2N in a final volume of 200 µl.

The results of these experiments demonstrate the specificity of the assay since only TLR9$^{YFP}$ binding to CpG-DNA was detected at a level above control and significant binding of TLR4$^{YFP}$ was not observed (FIG. 3A). Such assays can be modified for testing the ability of a compound to modulate the interaction between the TLR and a TLR-interactor (e.g., ligand). In addition, the ability of a molecule suspected of being able to interact with a TLR can be tested. For example, the compound can be biotinylated using methods known in the art and binding the biotinylated molecule to the plate instead of, e.g., biotinylated CpG-DNA.

In another design of the plate assay, anti-GFP coated microtiter plates (Pierce) were used to immobilize the TLR-fluorescent protein fusion protein and were used directly after coating with the TLR. The plates were incubated with cell lysates prepared from cells that stably express TLR9$^{YFP}$ or TLR4$^{YFP}$ for one hour at room temperature, washed three times with PBS/Tween 20 (0.05%), and then incubated with biotinylated CpG-DNA (2006); 0.01 µM) for one hour at room temperature, and washed again three times with PBS/Tween 20 (0.05%). Bound ligand was detected by incubating the plates with HRP-conjugated streptavidin for one hour at room temperature, washing with PBS/Tween 20 (0.05%), and detecting using HRP substrate (R and D) and determining the absorbance at 450 nm. The results of these experiments were similar to those in which the CpG-DNA was the immobilized component of the assay in that significant binding was observed only when the two interactants were CpG-DNA and TLR9$^{YFP}$ (FIG. 3B).

This assay can be adapted for use in drug-screening applications. For example, the interaction of TLR9 with CpG-DNA reflects a clinically important receptor/ligand interaction since a variety of autoimmune diseases are thought to be based on the interaction of DNA-antibody complexes with this receptor (Leadbetter et al., 2002, Nature 416:603-607). Thus, antagonists for this interaction are useful for the development of novel anti-inflammatory drugs. To examine the application of this assay to the identification of such compounds (e.g., compounds that increase or decrease the interaction) and so are potential drugs for ameliorating TLR-related disorders, a competition assay was developed that was based on the basic plate assay described above. The competition assay was performed essentially as described above for the plate assay. In addition, non-biotinylated CpG-DNA ("cold ligand") or other compounds that interfere with TLR9 signaling (R848 or bacterial DNA) were added to the TLR9-containing lysates. The ability of the various compounds to inhibit binding of TLR9$^{YFP}$ to the plate-bound biotinylated CpG-DNA was then evaluated. Since the ability of various compounds to inhibit binding was observed, these data demonstrate that the assay can be used to identify compounds that modulate the interaction of a TLR with a TLR interactor.

Example 2

Binding of CpG-DNA to TLR-9 is Saturable

Experiments were performed to determine the affinity of TLR9 to CpG-DNA (2006). In these experiments cellular lysates were prepared from HEK-TLR9$^{YFP}$ cells. NeutrAvidin™ microtiter plates (Pierce) were coated with various concentrations of CpG-DNA (2006) and incubated with the cellular lysates. After washing, the plates were incubated with anti-GFP monoclonal GFP, washed, incubated with anti-mouse-HRP, then detected with a color reaction to detect HRP activity. Absorbance was measured at 450 nm. The results of the experiments are shown in FIG. 4.

Binding of TLR9 to CpG-DNA was saturated at approximately 0.3 µM CpG-DNA and half-maximal binding was observed at 0.02 µM. Thus, the Kd of human TLR9 for CpG-DNA (2006-sequence) is around 20 nM (FIG. 4).

These data demonstrate that the characteristics of binding of a TLR to a TLR-interactor can be assayed using the plate assay. Such assays can also be used to evaluate the effects of a compound on the interaction between TLR and a TLR-interactor by either incubating a compound in the ligand-coated plate before adding the TLR or adding the compound with the TLR then assaying the amount of TLR associated with the ligand as described above and comparing the amount of association in the presence and absence of the compound. A decrease in the amount the association between TLR and the TLR-interactor in the presence of the compound indicates that the compound can decrease the interaction. A further variation on the assay is addition of the compound to the coated plate after the plate has been incubated with the TLR. Various concentrations of the compound are used or the compound can be added for various times. The assay is then carried out as described above. The results demonstrate the ability of the compound to displace the TLR in its interaction with the TLR interactor (e.g., ligand).

Example 3

Non-labeled CpG-DNA Competes for TLR9-CpG-DNA Interaction

One useful application of the TLR ligand binding assay is its use in drug-screening applications. For example, the interaction of TLR9 with CpG-DNA reflects a clinically important receptor/ligand interaction since a variety of auto-immune diseases are thought to be based on the interaction of DNA-antibody complexes with TLR9. Thus, antagonists for this interaction would obviously have a role in the development of novel anti-inflammatory drugs. To examine whether this assay is useful as a drug-screening assay, a competition assay was devised.

In the assay, NeutrAvidin™ plates (Pierce) were coated with 0.3 µM biotin-CpG-DNA 2006 as described above. Non-biotinylated CpG-DNA ("cold ligand"; CpG-DNA 2006 or CpG-DNA 1668, the mouse TLR9 optimal stimulating sequence) or other compounds that interfere with TLR9 signaling (R848 and bacterial DNA) were added to TLR9$^{YFP}$-containing cell lysates. These lysates were then added to the plate bound biotinylated CpG-DNA and processed as described above to detect the amount of binding of TLR9$^{YFP}$ bound to the plates.

The drug R848 inhibited TLR9 signaling in a dose dependent manner in TLR9—expressing HEK cells but did not interfere with the binding of TLR9 to CpG-DNA (FIGS. 5A-D). Genomic bacterial DNA in its unprocessed form did not induce TLR9 signaling in these experiments. Finally, when two different CpG-oligonucleotides were incubated with increasing concentrations of non-biotinylated CpG-DNA (2006 or 1668 sequence), dose dependent inhibition of TLR9 binding to biotinylated immobilized CpG-DNA was observed.

These data demonstrate that assays such as those described herein (e.g., a plate assay) can be used to test the ability of a compound to modulate the interaction between a TLR and TLR-interactor (e.g., a TLR ligand).

Example 4

Purification of TLR Fusion Proteins

In some cases, the use of a purified TLR, e.g., TLR-fluorescent fusion protein (TLR$^{FFP}$), is used. Purified proteins can improve the sensitivity of the assay system. For example, after preparing a cell lysate from a cell line that stably expresses a TLR9$^{GFP}$, the fusion protein is purified by affinity chromatography. In a typical purification protocol, an anti-GFP antibody is immobilized on a solid matrix using common established protocols (column resins such as activated agarose beads, are commercially available from several companies such as Pierce and Amersham). The TLR9$^{GFP}$ containing cellular lysate is then mixed with the antibody containing beads for one hour at 4° C. Beads are then extensively washed in lysis buffer and purified TLR9 eluted in low pH (glycine buffer pH 2.2).

Example 5

Amplified Luminescent Proximity Homogenous Assay (ALPHA)

To demonstrate the use of the Perkin Elmer AlphaScreen™ assay technology (illustrated in FIG. 6A) for the probing of receptor/ligand interaction of TLRs, the assay was performed with a purified TLR9-Fc fusion protein and biotinylated DNA. 10 µg/ml purified TLR9-Fc protein was incubated with increasing doses of biotinylated CpG-DNA for 1 hour in the wells of a 385 well plate. Thereafter, streptavidin-coated donor beads and protein A-coated acceptor beads were added and the mixture was incubated for another hour at room temperature. The buffer system used for this assay was as follows: MES 50 mM, NaCl 150 mM, CaCl$_2$ 1 mM, 0.1% BSA, 0.01% Tweenrm 20, pH6.

FIG. 6B shows a representative experiment of CpG-DNA/TLR9-Fc interaction. Two kinds of DNA were interacted with TLR9-FC in this experiment. The 2006 sequence (described above) and the 2006GC sequence. The ligand was titrated over a range of 0.01 nM to 1000 nM. The bell-shaped curves that were obtained represent both binding of DNA to TLR9-FC up to saturation of the beads (maximal AlphaScreen units) and blocking of the assay signal by excess ligand (downward slope of the curve after saturation). By adding excess ligand (more than the binding capacity of the streptavidin coated beads) one is able to obtain binding and blocking of the signal in the same experiment.

Example 6

TLR2 is Activated by PorinB in Living Cells

TLR2 binds and is triggered by a variety of bacterial derived molecular signatures, such as lipoproteins (proteins anchored to the bacterial wall via lipid anchors), outer membrane proteins (proteins involved in bacteria metabolism, such as ion channels) and peptidoglycan (the "fabric" of all bacteria's cell wall) (Beutler et al., 2003, J. Leukoc. Biol., 74(4):479-85).

Because of its wide range of ligands, TLR2 is an optimal candidate for screening for TLR interactors that are biologic response modifiers (Beutler, 2004, Nature, 430(6996):257-63), e.g., activators (e.g., vaccine adjuvants (Schjetne et al., 2003, J. Immunol., 171(1):32-6) and blockers (e.g., anti-inflammatory compounds (Meng et al., 2004, J. Clin. Invest., 113(10):1473-81)). In the following examples, we report a variety of binding assays involving the interaction of TLR2 with the protein PorinB from Neisseria meningitidis and a synthetic prototypic lipopeptide, Pam2CysK4.

293 cells stably expressing TLR4/MD-2 (as described in Visintin et al., 2003, J. Biol. Chem., 278(48):48313-48320) or TLR2 were stimulated using lipopolysaccharide (LPS) or PorinB, and the extent of activation measured as the activation of a NF-κB-dependent reporter gene encoding for the Luciferase gene. To measure NF-κB activation, 2 µg of a reporter plasmid in which NF-κB drives the synthesis of luciferase was transiently cotransfected with 5 µg of the indicated cDNA by lipofection (GeneJuice) in 10-cm tissue culture dishes following the manufacturer's recommendations. The following morning, cells were seeded at a density of 50,000 cells/well in a 96-well plate, allowed to recover for 5 hours, and stimulated as indicated between 6 and 18 hours. Luciferase activity was measured with a plate reader luminometer (Victor$^2$, PerkinElmer Life Sciences) using chemicals provided with the luciferase assay system (Promega, Madison, Wis.). All data are presented as the means ±S.D. of triplicate well readings, normalized to a value of 1.0 in comparison with an unstimulated negative control.

The results are shown in FIGS. 7A-B. The different gray tones correspond to the concentrations of stimulant used. LPS, a well known TLR4/MD-2 agonist, could activate TLR4/MD-2 (7A) expressing reporter cells, but failed to activate TLR2 expressing cells (7B). On the contrary, PorinB efficiently activates TLR2 expressing cells, but not TLR4/MD-2 reporter cells. This data demonstrates that PorinB is likely to interact with TLR2, and that this method can be used to assay receptor activation after stimulation with a ligand.

Example 7

TLR2 Binds to PorinB in Living Cells

In order to develop a binding assay for TLR2 and PorinB, the TLR protein was biotinylated using standard chemistry (Pierce Biotechnology, Inc., Rockford, Ill.). Briefly, adherent cells from a confluent 10-cm dish were labeled with biotin (Pierce) on ice, solubilized in detergent (1% Triton X-100, 10 mM Tris-Cl (pH 7.4), 137 mM NaCl, 10% glycerol, 2 mM EDTA, and protease inhibitors), subjected to immunoprecipitation with the appropriate antibodies (2 µg/ml) in 20 µl of packed protein A-Sepharose (Amersham Biosciences, Uppsala, Sweden) for 16 hours at 4° C., resolved by SDS-PAGE, and electro-transferred onto Hybond-C™ nitrocellulose membranes (Amersham Biosciences). The membranes were blocked in 5% dry milk in phosphate-buffered saline (PBS) and 0.1% Tween 20 for 30 minutes at 37° C. and probed for an additional 30 minutes at 37° C. with horseradish peroxidase-conjugated anti-biotin polyclonal antibody (1 µg/ml). Biotinylated proteins were revealed by enhanced chemiluminescence using a commercial kit for this purpose (Amersham Biosciences). When necessary, membranes were stripped for 30 min in 0.1 M glycine (pH 2.2), 1% Tween 20, and 0.1% SDS and reprobed.

In FIG. 7C, an anti biotin western immunoblotting performed on biotinylated Porin is shown to demonstrate essential purity of the preparation. The binding of Porin to living cells was then assessed, as shown in FIG. 7D. Adherent cells expressing a GFP-tagged TLR2 molecule were incubated with 10 mg/ml of biotinylated PorinB for different time periods and then extensively washed. Cells were solubilized in lysis buffer (10 mM Tris, pH 7.4, 137 mM NaCl, 0.5% Triton X-100, 2 mM EDTA, 10% glycerol, and protease inhibitors) and biotin was captured with streptavidin beads. The pellets were then separated by electrophoresis and western blotted using an anti GFP monoclonal antibody to reveal TLR2 (enhanced chemiluminescence, Amersham-Pharmacia).

These results demonstrate that this method can be used for the screening of molecules that can interfere with the binding of a ligand, e.g., biotinylated PorinB to living cells expressing a tagged version of a TLR, e.g., TLR2. Other ligands and TLRs can also be used.

Example 8

TLR2 Binds to PorinB in Cell-Free Systems

The binding of TLR2 ligands was assessed by ELISA in a cell free system.

Briefly, various TLR2 ligands were plated on plastic in carbonate buffer pH 9 for two hours at different concentrations (X axis) in duplicate points. After washing (PBS-0.05% Tween 20), a fusion protein consisting of the extracellular domain of TLR2 and the mouse Fc portion of immunoglobulin G, isotype 2a (TLR2:Fc, see U.S. Provisional Patent Application Ser. No. 60/598,774), was added at 1 mg/ml (0.1 mg/well). After extensive washing, the bound TLR2:Fc protein was revealed by incubation with a HRP conjugated anti mouse polyclonal antiserum and the ELISA developed using standard chromogenic substrates for the enzyme HRP.

The results, shown in FIG. 8A, demonstrate that this assay can be used to determine binding of various ligands to TLRs in vitro.

In a similar setting, the TLR2:Fc fusion protein and the related TLR4:Fc, were plated on plastic and the biotinylated ligand used to probe the wells. The TLR2 bound biotinylated protein was reveled using a HRP conjugated anti biotin polyclonal antiserum (NEB).

The results are shown in FIG. 8B. TLR2 specifically bound to biotinylated PorinB, whereas the TLR4 fusion protein did not.

Thus, these methods allow the screening of TLR2 interactors in a multiwell format, which can be easily handled by robotic liquid handlers, providing for high-throughput assays.

Example 9

TLR4 Binds to LPS in Cell-Free Systems

TLR4 is the receptor responsible for activating cells in response to lipopolysaccharide (LPS) challenge. It is a typical TLR, in that it has a LRR extracellular domain and an intracellular TIR. TLR4 can sense LPS only when in the presence of MD-2, a secreted 160 amino acid glycoprotein that associates with the extracellular domain of TLR4. LPS is thought to interact with both TLR4 and MD-2. MD-2 is a stand alone LPS receptor, as it can bind to LPS without TLR4. However, TLR4 cannot interact with LPS in the absence of MD-2 (Visintin et al., 2003, supra).

B1287 is a synthetic LPS analog developed by Eisai Research Institute (Andover, Mass.; see International Patent Application No. WO-9639411-A1); see Ingalls et al., 1998, J. Immunol., 161:5413-5420. This compound antagonizes the effects of LPS; as the mechanism is by preventing the interaction of MD-2 and TLR4 with LPS.

Figure 9:
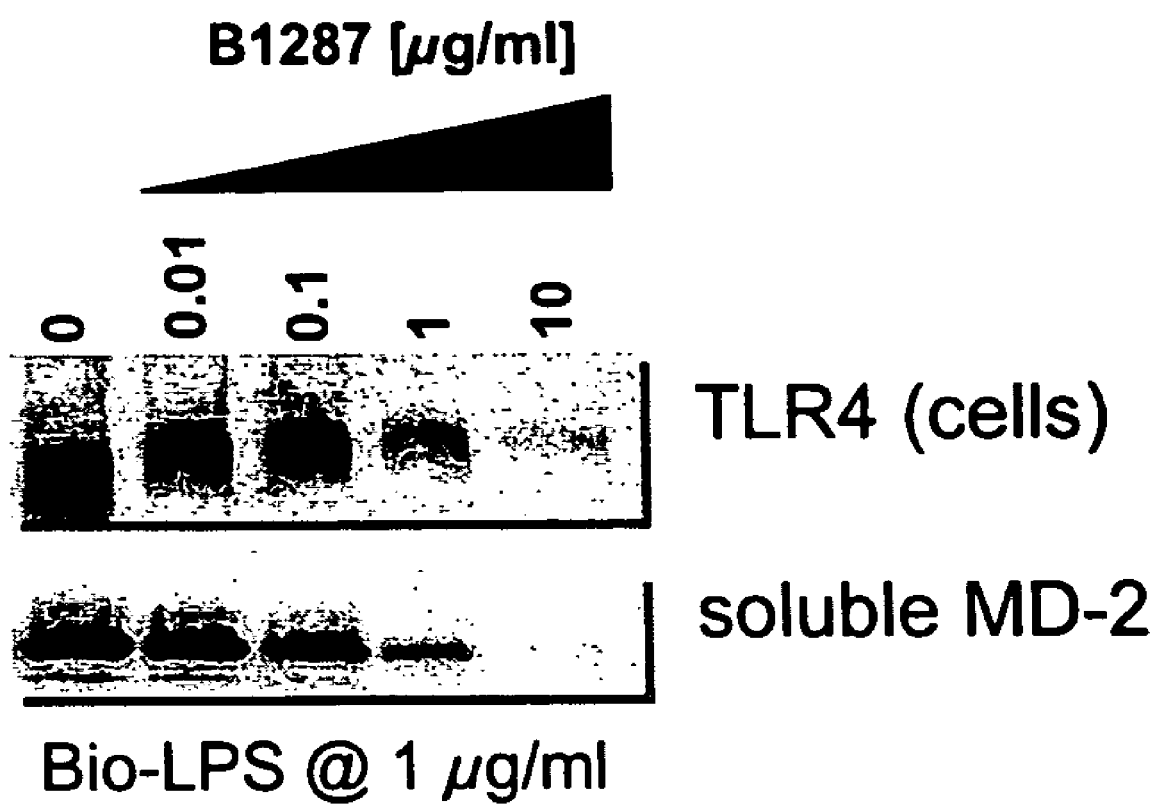
FIG. 9 is a pair of Western blots showing the effect of increasing concentrations of B1287, an LPS antagonist, on binding of biotinylated LPS to cell-surface TLR4 (top panel) and soluble MD-2 (bottom panel).

Briefly, cells expressing a GFP tagged TLR4 chimeric protein were incubated with fixed amounts of biotinylated LPS (1 mg/ml) and increasing amounts of the LPS antagonist B1287 for one hour at the indicated concentrations. The results are shown in FIG. 9, top panel. At 0 competitor (lane 1), the binding is maximal, and the avidin beads could precipitate biotinylated LPS and the associated TLR4$^{GFP}$ molecule, as revealed by western blotting for GFP. However, B1287 could efficiently prevent the interaction of TLR4 and LPS, thus preventing the formation of a precipitable complex containing TLR4, in a dose dependent manner. At a concentration roughly 10 fold the LPS (in weight), the competitor could completely block the interaction. This method can be used to screen for LPS antagonists/agonists (TLR4 interactors) in living cells.

In a parallel experiment (FIG. 9, lower panel), supernatants from the same cells in A were precipitated using streptavidin beads and the presence of LPS bound MD-2 was assessed in the pellets by anti FLAG western blotting. As expected, the LPS antagonist B1287 could efficiently prevent the interaction of LPS with MD-2 as well.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of identifying a compound that modulates binding of a cognate ligand to Toll-like receptor 2 (TLR2), the method comprising:
   (a) providing a sample comprising a chimeric polypeptide comprising a TLR2 polypeptide or ligand-binding fragment thereof, and a fluorescent protein;
   (b) contacting the sample with a cognate TLR2 ligand and a test compound, thereby forming a test sample;
   (c) incubating the test sample for a time and under conditions sufficient for the TLR2 ligand to bind to the TLR2 polypeptide in the absence of the test compound; and
   (d) determining binding between the TLR2 polypeptide and the TLR2 ligand in the test sample,
   wherein the TLR2 ligand is bound to a bead and wherein a difference in binding in the test sample compared to a control indicates that the test compound is a candidate compound for modulating binding of a cognate ligand to TLR2.

2. The method of claim 1, wherein the TLR2 ligand or the TLR2 polypeptide is biotinylated.

3. The method of claim 1, wherein the fluorescent protein is Green fluorescent protein (GFP) or a fluorescent variant thereof.

4. The method of claim 1, wherein the TLR2 ligand is biotinylated and the bead comprises avidin, streptavidin, or a deglycosylated form of avidin.

5. The method of claim 1, wherein the TLR2 polypeptide is bound to a solid surface.

6. The method of claim 5, wherein the TLR2 polypeptide is biotinylated and the solid surface comprises avidin, streptavidin, or a deglycosylated form of avidin.

7. The method of claim 1, wherein one or more of the TLR2 polypeptide and the TLR2 ligand is labeled.

8. The method of claim 7, wherein the label comprises europium or allophycocyanin.

9. The method of claim 1, wherein the binding between the TLR2 polypeptide and TLR2 ligand is detected by time resolved fluorimetry.

10. The method of claim 1, wherein the binding between the TLR2 polypeptide and the TLR2 ligand is detected with an antibody that specifically binds to the TLR2 polypeptide.

11. The method of claim 10, wherein the antibody is labeled with a lanthanide chelate fluorophore and time-resolved fluorimetry is used to detect the binding.

12. The method of claim 1, wherein a test compound that decreases the binding between the TLR2 polypeptide and the TLR2 ligand is a candidate compound for inhibiting binding of cognate ligand to TLR2.

13. The method of claim 1, wherein a test compound that increases the binding between the TLR2 polypeptide and the TLR2 ligand is a candidate compound for increasing binding of cognate ligand to TLR2.

14. The method of claim 1, wherein the sample further comprises a Toll-like receptor 1 (TLR1) polypeptide, a Toll-like receptor 6 (TLR6) polypeptide, or both.

* * * * *